United States Patent
Xie et al.

(10) Patent No.: US 12,383,652 B2
(45) Date of Patent: Aug. 12, 2025

(54) NANOFIBER STRUCTURES AND METHODS OF MANUFACTURE AND USE THEREOF

(71) Applicant: BOARD OF REGENTS OF THE UNIVERSITY OF NEBRASKA, Lincoln, NE (US)

(72) Inventors: Jingwei Xie, Omaha, NE (US); Shixuan Chen, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 838 days.

(21) Appl. No.: 17/413,147

(22) PCT Filed: Dec. 16, 2019

(86) PCT No.: PCT/US2019/066495
§ 371 (c)(1),
(2) Date: Jun. 11, 2021

(87) PCT Pub. No.: WO2020/124072
PCT Pub. Date: Jun. 18, 2020

(65) Prior Publication Data
US 2022/0023496 A1   Jan. 27, 2022

Related U.S. Application Data

(60) Provisional application No. 62/779,564, filed on Dec. 14, 2018.

(51) Int. Cl.
| | | |
|---|---|---|
| *A61L 27/18* | (2006.01) | |
| *A61P 19/00* | (2006.01) | |
| *B82Y 40/00* | (2011.01) | |
| *C12N 5/077* | (2010.01) | |
| *D01D 5/00* | (2006.01) | |

(52) U.S. Cl.
CPC ............. *A61L 27/18* (2013.01); *A61P 19/00* (2018.01); *C12N 5/0656* (2013.01); *D01D 5/0007* (2013.01); *A61L 2430/02* (2013.01); *B82Y 40/00* (2013.01); *C12N 2513/00* (2013.01); *C12N 2533/30* (2013.01); *C12N 2535/00* (2013.01); *D10B 2331/041* (2013.01)

(58) Field of Classification Search
CPC ...................................................... A61L 27/18
See application file for complete search history.

(56) References Cited

U.S. PATENT DOCUMENTS

| | | |
|---|---|---|
| 3,674,540 A | 7/1972 | Pergaminos |
| 6,653,005 B1 | 11/2003 | Muradov |
| 7,465,784 B2 | 12/2008 | Wang |
| 7,704,740 B2 | 4/2010 | Schindler et al. |
| 9,403,958 B2 | 8/2016 | Lindner et al. |
| 9,580,472 B2 | 2/2017 | Wang |
| 9,655,995 B2 | 5/2017 | Xie |
| 9,913,862 B2 | 3/2018 | Collins et al. |
| 10,144,767 B2 | 12/2018 | Wang |
| 10,799,620 B2 | 10/2020 | Xie et al. |
| 11,033,659 B2 | 6/2021 | Xie et al. |
| 11,318,224 B2 | 5/2022 | Xie et al. |
| 11,427,936 B2 | 8/2022 | Xie |
| 2005/0084532 A1 | 4/2005 | Howdle et al. |
| 2005/0187330 A1 | 8/2005 | Gulari et al. |
| 2006/0002978 A1 | 1/2006 | Shea et al. |
| 2007/0077272 A1 | 4/2007 | Li et al. |
| 2008/0112998 A1 | 5/2008 | Wang |
| 2009/0156499 A1 | 6/2009 | Wang |
| 2010/0183699 A1 | 7/2010 | Wan et al. |
| 2011/0070151 A1 | 3/2011 | Braithwaite et al. |
| 2011/0195123 A1 | 8/2011 | Shemi |
| 2011/0293685 A1 | 12/2011 | Kuo et al. |
| 2012/0040581 A1 | 2/2012 | Kim |
| 2012/0226295 A1 | 9/2012 | Jabbari |
| 2013/0095167 A1 | 4/2013 | Warnke |
| 2013/0112625 A1 | 5/2013 | Bahukudumbi et al. |
| 2014/0024760 A1 | 1/2014 | Kwon et al. |
| 2014/0051169 A1 | 2/2014 | Ganey et al. |
| 2014/0303069 A1 | 10/2014 | Wang et al. |
| 2015/0259382 A1 | 9/2015 | Wang |
| 2016/0015792 A1 | 1/2016 | Hendricus van Pinxteren et al. |
| 2016/0015952 A1 | 1/2016 | Omachi et al. |
| 2016/0106548 A1 | 4/2016 | Li et al. |
| 2016/0176714 A1 | 6/2016 | Do et al. |
| 2017/0296703 A1 | 10/2017 | Xie et al. |
| 2018/0028317 A1 | 2/2018 | Schlachter |
| 2019/0209732 A1 | 7/2019 | Xie et al. |
| 2020/0164107 A1 | 5/2020 | Xie et al. |

(Continued)

FOREIGN PATENT DOCUMENTS

| | | |
|---|---|---|
| CN | 102068716 A | 5/2011 |
| CN | 102071485 A | 5/2011 |

(Continued)

OTHER PUBLICATIONS

Jiang, J. et al., Expanded 3D nanofiber scaffolds: cell penetration, neovascularization, and host response, Advanced Healthcare Materials, 2016, vol. 5, 2993-3003 (Year: 2016).*
Pan, J.F. et al., Preparation and characterization of electrospun PLCL/Poloxamer nanofibers and dextran/gelatin hydrogels for skin tissue engineering, PLOS One, Nov. 18, 2014, vol. 9, 12 pages (Year: 2014).*
Dumortier, G. et al., A review of poloxamer 407 pharmaceutical and pharmacological characteristics, Pharmaceutical Research, Nov. 11, 2006, vol. 23, 2709-2728 (Year: 2006).*
Xie, J. et al., Putting electrospun nanofibers to work for biomedical research, Macromolecular Rapid Communications, 2008, vol. 29, 1775-1792 (Year: 2008).*
Sun, B. et al., Development of nanofiber spondges-containing nerve guidance conduit for peripheral nerve regeneration in vivo, ACS Applied Materials & Interfaces, Jul. 18, 2017, vol. 9, 26684-26696 (Year: 2017).*

(Continued)

*Primary Examiner* — Craig D Ricci
*Assistant Examiner* — Paul Hoerner
(74) *Attorney, Agent, or Firm* — Robert C. Netter, Jr.; Dann, Dorfman, Herrell & Skillman

(57) ABSTRACT

Nanofiber structures are provided as well as methods of use thereof and methods of making.

46 Claims, 27 Drawing Sheets

Specification includes a Sequence Listing.

(56) References Cited

U.S. PATENT DOCUMENTS

| | | |
|---|---|---|
| 2020/0277711 A1 | 9/2020 | Xie |
| 2021/0268154 A1 | 9/2021 | Xie et al. |
| 2022/0226537 A1 | 7/2022 | Xie et al. |

FOREIGN PATENT DOCUMENTS

| | | | |
|---|---|---|---|
| CN | 102703996 A | 10/2012 | |
| CN | 103382625 A | 11/2013 | |
| CN | 104464712 A | 3/2015 | |
| CN | 106421898 A | 2/2017 | |
| CN | 106492289 A | 3/2017 | |
| CN | 106563172 A | 4/2017 | |
| CN | 106620881 A | 5/2017 | |
| CN | 105012991 B | 1/2018 | |
| EP | 1611877 A1 | 1/2006 | |
| EP | 2813212 A1 | 12/2014 | |
| JP | 2006-169497 A | 6/2006 | |
| JP | 2007160691 A | 6/2007 | |
| JP | 2007222477 A | 9/2007 | |
| JP | 4656320 B2 | 3/2011 | |
| KR | 101493444 B1 | 2/2015 | |
| WO | 00/50104 A1 | 8/2000 | |
| WO | 2006/019600 A2 | 2/2006 | |
| WO | 2018/227078 A1 | 12/2008 | |
| WO | 2009/011658 A1 | 1/2009 | |
| WO | 2009/088777 A1 | 7/2009 | |
| WO | 2014/037651 A1 | 3/2014 | |
| WO | 2014/191739 A1 | 12/2014 | |
| WO | 2015/051042 A2 | 4/2015 | |
| WO | WO-2016053988 A1 * | 4/2016 | ........... A61K 9/0092 |
| WO | 2018/064281 A1 | 4/2018 | |
| WO | 2019/060393 A1 | 3/2019 | |
| WO | 2019209762 A1 | 10/2019 | |
| WO | 2020/076381 A1 | 4/2020 | |
| WO | 2020/159946 A1 | 8/2020 | |

OTHER PUBLICATIONS

Chen, S.-H et al., Prevention of peritendinous adhesions with electrospun chitosan-grafted polycaprolactone nanofibrous membranes, Acta Biomaterialia, Sep. 2, 2014, vol. 10, 4971-4982 (Year: 2014).*

Chen, et al., "Three-Dimensional Objects Consisting of Hierarchically Assembled Nanofibers with Controlled Alignments for Regenerative Medicine" Nano Lett. (2019) 19(3):2059-2065.

Kang, et al., "Chitosan-coated poly(vinyl alcohol) nanofibers for wound dressings" J. Biomed. Mater. Res. B Appl. Biomater. (2010) 92(2):568-76.

Chen, et al., "Fabrication of Injectable and Superelastic Nanofiber Rectangle Matrices ("Peanuts") and Their Potential Applications in Hemostasis" Biomaterials (2018) 179:46-59.

Liu, Y., et al., "HB-EGF embedded in PGA/PLLA scaffolds via subcritical CO2 augments the production of tissue engineered intestine" Biomaterials (2016) 103:150-159.

Geiger, B.C., et al., "Dual Drug Release from CO2-Infused Nanofibers via Hydrophobic and Hydrophilic Interactions" J. Appld. Polymer Sci. (2015) 132(38):42571.

Ayodeji, O., et al., "Carbon dioxide impregnation of electrospun polycaprolactone fibers" J. Supercritical Fluids (2007) 41:173-178.

Jiang, J., et al., "CO2-Expanded Nanofiber Scaffolds Maintain Activity of Encapsulated Bioactive Materials and Promote Cellular Infiltration and Positive Host Response" Acta Biomater. (2018) 68:237-248.

Nazarov, R., et al., "Porous 3-D scaffolds from regenerated silk fibroin" Biomacromolecules (2004) 5(3):718-26.

Joshi, M.K., et al., "Multi-layered macroporous three-dimensional nanofibrous scaffold via a novel gas foaming technique" Chem. Engr. J. (2015) 275:79-88.

Bencherif, S.A., et al., "Advances in the design of macroporous polymer scaffolds for potential applications in dentistry" J. Periodontal Implant Sci. (2013) 43(6):251-61.

Xie, J., et al., "Putting Electrospun Nanofibers to Work for Biomedical Research" Macromol. Rapid Commun. (2008) 29:1775-1792.

Jiang, J., et al., "Expanding Two-Dimensional Electrospun Nanofiber Membranes in the Third Dimension By a Modified Gas-Foaming Technique" ACS Biomater. Sci. Eng. (2015) 1(10):991-1001.

Liu, W., et al., "Electrospun nanofibers for regenerative medicine" Adv. Healthc. Mater. (2012) 1(1):10-25.

Nam, Y.S., et al., "A Novel Fabrication Method of Macroporous Biodegradable Polymer Scaffolds Using Gas Foaming Salt as a Porogen Additive" J. Biomed. Mater. Res. (2000) 53(1):1-7.

Lee, Y.H., et al., "Electrospun dual-porosity structure and biodegradation morphology of Montmorillonite reinforced PLLA nanocomposite scaffolds" Biomaterials (2005) 26:3165-3172.

Jiang, J., et al., "Local Sustained Delivery of 25-Hydroxyvitamin D3 for Production of Antimicrobial Peptides" Pharm. Res. (2015) 32(9): 2851-2862.

Ma, B., et al., "Rational design of nanofiber scaffolds for orthopedic tissue repair and regeneration" Nanomedicine (2013) 8(9):1459-81.

Dehghani, et al., "Engineering porous scaffolds using gas-based techniques" Current Opinion in Biotechnology (2011) 22:661-666.

Mulmi, et al., "Fabrication of Air Freshening Spongy Three Dimensional Electrospun Membrane" Journal of the Institute of Engineering (2018) 14(1):14-21.

Keit, et al., "Expansion of Two-dimension Electrospun Nanofiber Mats into Three-dimension Scaffolds" J. Vis. Exp. (2018):e58918.

Liu, Y., et al., "Composite vascular scaffold combining electrospun fibers and physically-crosslinked hydrogel with copper wire-induced grooves structure" J. Mech. Behav. Biomed. Mater. (2016) 61:12-25.

Zhao, Y., et al., "Preparation of Nanofibers with Renewable Polymers and Their Application in Wound Dressing" Intl. J. Polmer Sci. (2016) 2016:4672839.

Pok, S., et al., "A multilayered scaffold of a chitosan and gelatin hydrogel supported by a PCL core for cardiac tissue engineering" Acta Biomater. (2013) 9(3):5630-5642.

Xie, J, et al., "Controlled biomineralization of electrospun poly(ε-caprolactone) fibers for enhancing their mechanical properties" Acta Biomaterialia (2013) 9(3):5698-5707.

Xie, J., et al., "The differentiation of embryonic stem cells seeded on electrospun nanofibers into neural lineages" Biomaterials (2009) 30(3):354-362.

Chen, S., et al., "Recent advances in electrospun nanofibers for wound healing" Nanomedicine (Lond.) (2017) 12 (11):1335-1352.

Electrospin Tech, "Post-electrospinning expansion of 2D membrane to 3D scaffold using gas foaming" (Oct. 27, 2015) available at: http://electrospintech.com/gasfoam3d.html#.X5bnPC9h0kg.

Borjigin, M., et al., "Proliferation of Genetically Modified Human Cells on Electrospun Nanofiber Scaffolds" Mol. Ther.-Nuc. Acids (2012) 1:e59.

Lee, S.J., et al., "The use of thermal treatments to enhance the mechanical properties of electrospun poly(E-caprolactone) scaffolds" Biomaterials (2008) 29:1422-1430.

Xie, J., et al., "Electrospray in the dripping mode for cell microencapsulation" J. Colloid Interface Sci. (2007) 312:247-255.

Cai, H., et al., "Aerogel Microspheres from Natural Cellulose Nanofibrils and Their Application as Cell Culture Scaffold" Biomacromolecules (2014) 15:2540-2547.

Hiwang, P.T.J., et al., "Poly(ε-caprolactone)/gelatin composite electrospun scaffolds with porous crater-like structures for tissue engineering" J Biomed Mater Res A. (2016) 104(4):1017-1029.

Wang, W., et al., "Dentin regeneration by stem cells of apical papilla on injectable nanofibrous microspheres and stimulated by controlled BMP-2 release" Acta Biomater. (2016) 36:63-72.

Gu, B.K., et al., "Fabrication of sonicated chitosan nanofiber mat with enlarged porosity for use as hemostatic materials" Carbohydr. Polym. (2013) 97(1):65-73.

Jiang, J., et al., "Expanded Three-dimensional Nanofiber Scaffolds: Cell Penetration, Neovascularization, and Host Response" Adv. Healthc. Mater. (2016) 5(23): 2993-3003.

Gao, Q., et al., "Fabrication of electrospun nanofibrous scaffolds with 3D controllable geometric shapes" Mater. Design (2018) 157:159-169.

(56) References Cited

OTHER PUBLICATIONS

Boda, S.K., et al., "Electrospraying Electrospun Nanofiber Segments into Injectable Microspheres for Potential Cell Delivery" ACS Appl. Mater. Interfaces (2018) 10:25069-25079.

Boda, S.K., et al., "Mineralized nanofiber segments coupled with calcium-binding BMP-2 peptides for alveolar bone regeneration" Acta Biomater. (2019) 85:282-293.

Fu, L., et al., "Three-dimensional nanofiber scaffolds with arrayed holes for engineering skin tissue constructs" MRS Communications (2017) 7:361-366.

Wei, et al., "The multifunctional wound dressing with core-shell structured fibers prepared by coaxial electrospinning" Front. Mater. Sci. (2016) 10(2):113-121.

Su, et al., "Nanofiber Dressings Topically Delivering Molecularly Engineered Human Cathelicidin Peptides for the Treatment of Biofilms in Chronic Wounds" Mol. Pharmaceutics (2019) 16:2011-2020.

Su, et al., "Dissolvable Microneedles Coupled with Nanofiber Dressings Eradicate Biofilms via Effectively Delivering a Database-Designed Antimicrobial Peptide" ACS Nano (2020) 14(9):11775-11786.

\* cited by examiner 4 weeks 4 weeks 8 weeks 8 weeks

NANOFIBER STRUCTURES AND METHODS OF MANUFACTURE AND USE THEREOF

This application is a § 371 application of PCT/US2019/066495, filed Dec. 16, 2019, which claims priority under 35 U.S.C. § 119 (e) to U.S. Provisional Patent Application No. 62/779,564, filed Dec. 14, 2018. The foregoing applications are is incorporated by reference herein.

This invention was made with government support under Grant Nos. R01 GM123081 and R21 DE027516 awarded by the National Institutes of Health. The government has certain rights in the invention.

FIELD OF THE INVENTION

This application relates to the fields of nanofiber structures. More specifically, this invention provides methods of synthesizing nanofiber structures and methods of use thereof.

BACKGROUND OF THE INVENTION

Several publications and patent documents are cited throughout the specification in order to describe the state of the art to which this invention pertains. Each of these citations is incorporated herein by reference as though set forth in full.

Complex three-dimensional (3D) assembly of nanofibers represents ubiquitous extracellular matrix (ECM) in most human tissues (Stevens, et al. (2005) Science 18:1135-1138). Nanofiber scaffolds have been widely used to mimic the architecture of ECM in native tissues (Wang, et al. (2018) Sci. Adv. 4:eaat4537; MacQueen, et al. (2018) Nat. Biomed. Eng., 2(12):930-941; Carlson, et al. (2016) Nat. Commun., 7:10862; Chen, et al. (2018) Adv. Drug Del. Rev., 132:188-213). However, it is difficult to make complex 3D shapes composed of thin and flexible nanofiber films with thickness in the range of micrometer scale despite of emergence of 3D microfabrication techniques. Recent studies reported an Origami or Kirigami, ancient paper folding and/or cutting, inspired approach to transform two-dimensional (2D) films to 3D structures (Xu, et al. (2015) Science 347:154-159; Zhang, et al. (2015) Proc. Natl. Acad. Sci., 112:11757-11764; Yan, et al. (2016) Sci. Adv. 2:e1601014; Nan, et al. (2017) Adv. Funct. Mater. 27:1604281; Callens, et al. (2018) Mater. Today 21:241-264; Fu, et al. (2018) Nat. Mater., 17:268-276). However, such approaches are restrained to rolling, bending, folding, wrinkling, or buckling for transformation of 2D films to 3D structures. These methods have not been successfully used to transform 2D nanofiber films to 3D structures. Researchers also attempted to control the deposition of fibers to form 3D structures during the electrospinning process (Brown, et al. (2011) Adv. Mater., 23:5651-5657; Lee, et al. (2014) Langmuir 30:1210-1214; Luo, et al. (2015) ACS Appl. Mater. Interfaces 7:27765-27770). However, only some simple 3D architectures including grids, walls, and hollow cylinders have been generated to date. Moreover, the direct electrospinning of fibers into controllable 3D architectures is still in an initial stage facing many technological issues. Combining 3D printing and melt electrospinning can only produce 3D microfiber patterns with limited thickness (normally less than several mm) This method is associated with complicated equipment and is time consuming. In addition, the deposited fibers were mainly in micrometer scale instead of nanometer scale. Accordingly, new methods for the fabrication of nanofiber structures are needed.

SUMMARY OF THE INVENTION

In accordance with the instant invention, nanofiber structures and methods of producing the nanofiber structures are provided. In a particular embodiment, the nanofiber structures comprise an expanded, nanofiber structure comprising a plurality of nanofibers. In a particular embodiment, the nanofiber structures are synthesized by fixing (e.g., thermally fixing) at least one point of a nanofiber mat and expanding the fixed nanofiber mat by exposure to gas bubbles. In a particular embodiment, the nanofiber mat is expanded by exposure to a subcritical fluid such as subcritical $CO_2$ and then depressurized (e.g., within a container). The nanofiber structure may comprise a plurality of electrospun nanofibers (e.g., uniaxially-aligned, random, entangled, and/or electrospun fibers). The nanofiber structure may also comprise a material that enhances water absorption, such as gelatin, chitosan, or collagen. In a particular embodiment, the nanofiber structure is cross-linked. The nanofiber structure may also comprise cells and/or one or more agents or compounds such as therapeutic agents. In a particular embodiment, the nanofiber structure comprises a plurality of holes, particularly an array of holes.

In accordance with another aspect of the instant invention, methods of using the nanofiber structures are provided. For example, the nanofiber structures may be used to enhance wound healing, build tissue constructs, promote tissue regeneration (e.g., bone regeneration), reduce, inhibit, prevent, and/or eliminate infection, local delivery of drugs, and/or inhibit bleeding.

BRIEF DESCRIPTION OF THE DRAWINGS

FIG. 5A: The distribution of GFP-labeled human dermal fibroblasts in 1-mm-thickness expanded, radially aligned PCL nanofiber scaffold after culturing for 1 day and 3 days. FIG. 5B: The distribution of GFP-labeled dermal fibroblasts in 1-mm-thickness expanded, vertically aligned PCL nanofiber scaffold after culturing for 1 day and 3 days.

FIG. 6A: Hematoxyline and eosin (H&E) staining showing cell infiltration in expanded, radially-aligned PCL nanofiber scaffolds. FIG. 6B: H&E staining showing cell infiltration in expanded, vertically-aligned PCL nanofiber scaffolds. FIG. 6C: Collagen deposition and new blood vessels formation within expanded, radially-aligned PCL nanofiber scaffolds are shown. FIG. 6D: Collagen deposition and new blood vessel formation within expanded, vertically-aligned PCL nanofiber scaffolds are shown. Dots indicate the boundary between surrounding tissues and scaffolds.

FIG. 7A: H&E staining showing cell infiltration in expanded, radially-aligned PCL nanofiber scaffolds. FIG. 7B: H&E staining showing cell infiltration in expanded, vertically-aligned PCL nanofiber scaffolds. FIG. 7C: Collagen deposition and new blood vessels formation within expanded, radially-aligned PCL nanofiber scaffolds are shown. FIG. 7D: Collagen deposition and new blood vessel formation within expanded, vertically-aligned PCL nanofiber scaffolds are shown. Dots indicate the boundary between surrounding tissues and scaffolds.

FIG. 10A provides photographs of the implantation of radially aligned scaffolds (RAS) and vertically aligned scaffolds (VAS) as well as the defects without treatment as control. FIGS. 10B and 10C provide micro CT images of control, RAS and VAS groups after 4 and 8 weeks of implantation, respectively. FIGS. 10D and 10F provide the bone volume and FIGS. 10E and 10G provide the surface coverage of control, RAS and VAS groups after 4 and 8 weeks of implantation, respectively. FIG. 10H provides trichrome staining of control, RAS and VAS groups after 4 and 8 weeks implantation.

FIG. 11A provides photographs of implantation of low density, medium density and high density of vertically aligned scaffolds. FIGS. 11B and 11C provide micro CT images of low density, medium density and high density of vertically aligned scaffolds treated groups after 4 and 8 weeks of implantation, respectively. FIGS. 11D and 11F provide the bone volume and FIGS. 11E and 11G provide the surface coverage of low density, medium density and high density of vertically aligned scaffolds treated groups after 4 and 8 weeks of implantation, respectively. FIG. 11H provides trichrome staining of low density, medium density and high density of vertically aligned scaffolds treated groups after 4 and 8 weeks implantation.

FIG. 12A provides schematics of different types of two sides blocked 3D radially aligned scaffolds, including blocking the surrounding and top sides (block ST), blocking the surrounding and bottom sides (block SB), and blocking the top and bottom sides (block TB). FIG. 12B provides photographs of implantation of block ST, block SB, and block TB. FIGS. 12C and 12D provide micro CT images of block ST, block SB and block TB groups after 4 and 8 weeks of implantation, respectively. FIGS. 12E and 12G provide the bone volume and FIGS. 12F and 12H provide the surface coverage of block ST, block SB and block TB groups after 4 and 8 weeks of implantation, respectively. FIG. 12I provides trichrome staining of block ST, block SB and block TB groups after 4 and 8 weeks implantation.

DETAILED DESCRIPTION OF THE INVENTION

Figure 1A:
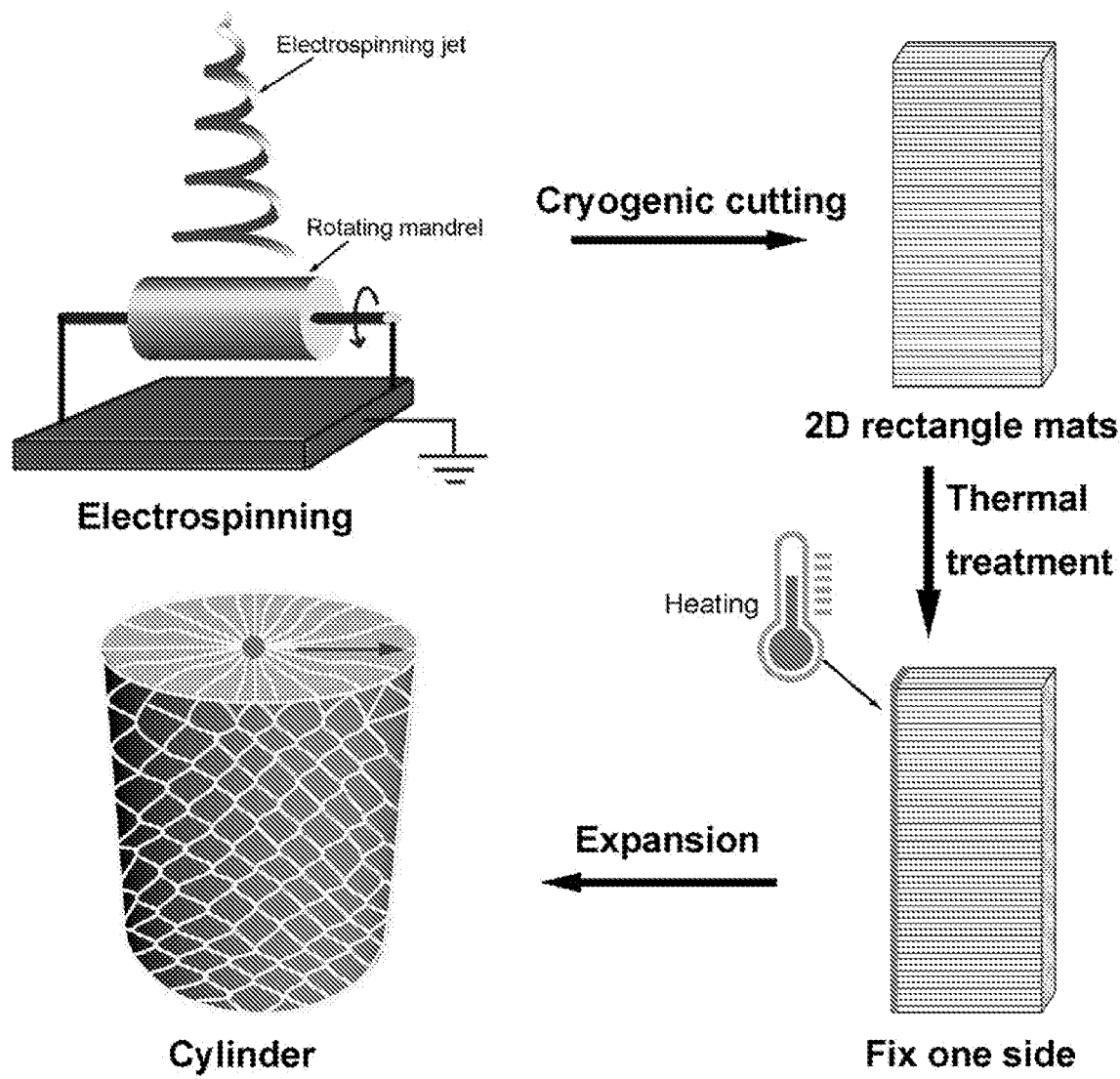
FIG. 1A provides a schematic illustrating the transformation of 2D nanofiber mats to predesigned 3D complex shapes. The 2D nanofiber mat is produced by electrospinning and collected on a rotating mandrel. The 2D nanofiber mat is then cut into a desired shape (e.g., rectangle) in liquid nitrogen. One side of the nanofiber mat is then fixed by thermal treatment. The nanofiber mat with one side fixed is expanded using a gas-foaming technique to form a 3D shape (e.g., a cylinder).

It is a great challenge to assemble pre-designed, 3D hierarchical structures of electrospun nanofibers with controlled orientations. Herein, a revolution-inspired strategy is used to transform 2D nanofiber mats with controlled thickness into pre-designed, complex 3D shapes, which were previously inaccessible. The synthesized 3D shapes can be highly porous consisting of aligned nanofiber layers with the gap distances of adjacent layers ranging from several microns to millimeters. The compressed, coated shapes are also capable of recovering to their original shapes. The assemblies can guide the organization of seeded cells to yield highly ordered 3D tissue constructs. In addition, subcutaneous implantation in rats demonstrates that nanofiber assemblies enable rapid cell penetration, new blood vessel formation, and collagen deposition. This new method of constructing 3D hierarchical architectures of nanofibers can be used for both in vivo tissue repair/regeneration and in vitro engineering complex 3D tissue constructs/models or organs.

3D scaffolds comprising hierarchically assembled nanofibers with controlled alignment are provided herein. The 3D scaffolds may be used, for example, for repair of tissues including bone defects (e.g., critical-sized bone defects such as cranial defects). The 3D scaffolds of the instant invention have many advantages. For example, the 3D scaffolds can be re-formulations of FDA-approved materials made into any unique structure for any purpose (e.g., for promoting bone regeneration). Moreover, it is shown herein that 2D nanofiber membranes can be used as a barrier to selectively block cell infiltration without influencing the diffusion of biomolecules secreted from cells. The methods of the instant invention allow for the fabrication of 3D objects of any size, thickness, and/or shape with controlled nanofiber alignment, pore size and/or porosity. Further, the 3D scaffolds of the instant invention are "self-fitting" in that they have excellent shape-memory and/or super-elastic properties. The 3D scaffolds also do not require the addition or incorporation of cells and/or therapeutics, although the 3D scaffolds are capable of incorporating cells and/or therapeutics. The methods of the instant invention can be scaled-up for mass production and the methods can be readily tailored to generate desired structures and compositions.

In accordance with the instant invention, methods of synthesizing expanded nanofiber (nanofibrous) structures (sometimes referred to as 3D scaffolds herein) are provided. It is envisioned that the expanded nanofiber structures of the present invention can be formed and manufactured into any shape, size, and/or thickness. For example, the expanded nanofiber structure may be a cylinder, cone, circular cone, sphere, hollow tube/cylinder, hollow sphere, bowl, etc.

The nanofibers of the instant invention can be fabricated by any method. In a particular embodiment, the expanded nanofiber structures comprise electrospun nanofibers. The expanded nanofiber structure may comprise aligned fibers (e.g., uniaxially aligned), random fibers, and/or entangled fibers. In a particular embodiment, the expanded nanofiber structure comprises aligned fibers (e.g., uniaxially, radially, vertically, or horizontally). While the application generally describes nanofibers (fibers having a diameter less than about 1 (e.g., average diameter)) structures and the synthesis of three-dimensional nanofibrous structures, the instant invention also encompasses microfibers (fibers having a diameter greater than about 1 (e.g., average diameter)) structures and the synthesis of three-dimensional microfibrous structures.

In certain embodiments of the instant invention, the methods comprise fixing at least one point, edge, end, or side—or a portion thereof—of a nanofiber mat (sometimes referred to as 2D structure herein) and then expanding the nanofiber mat into an expanded nanofiber structure (sometimes referred to as a 3D scaffold herein). In a particular embodiment, a whole or entire side of the nanofiber mat is fixed. In a particular embodiment, one or more sections or portions of the nanofiber mat is fixed (e.g., the top and bottom corners on one side may be fixed). The nanofiber mat may be fixed by any means. For example, the nanofiber mat may be thermally fixed or chemically fixed. In a particular embodiment, the nanofiber mat is thermally fixed.

In certain embodiments, the nanofiber mat is fixed by exposing at least one point, edge, end, or side—or a portion thereof—of the nanofiber mat to elevated temperatures. In a particular embodiment, the nanofiber mat is exposed to temperatures at or above the melting temperature of the nanofibers. In a particular embodiment, the nanofiber mat is fixed by exposing at least one point, edge, end, or side—or a portion thereof—of the nanofiber mat to a temperature of at least about 50° C., 55° C., 60° C., 65° C., 70° C., 75° C., 80° C., 85° C., 90° C., 95° C., 100° C., or higher. To avoid excess fixation and/or damage to the remainder of the nanofiber mat, the exposure to elevated temperatures may be brief (e.g., less than 10 seconds, less than 5 seconds, or for about 1 second). In a particular embodiment, the thermal fixing comprises exposing at least one point, edge, end, or side—or a portion thereof—of a nanofiber mat to about 75° C. to about 95° C., particularly about 85° C., for less than 5 seconds, particularly about 1 second.

In a particular embodiment, the nanofiber mat is chemically fixed, for example, by exposure to a chemical, solvent, or crosslinker. In a particular embodiment, a chemical or solvent based method is used to fix the nanofiber mat. The chemical or solvent used includes, but is not limited to: dichloromethane (DCM), dimethylformamide (DMF), dichloroformamide, acetone, and other organic solvents. In a particular embodiment, the nanofiber mat is fixed by exposure to a crosslinker. In a particular embodiment, the nanofiber mat is chemically fixed by exposing at least one point, edge, end, or side—or a portion thereof—of the nanofiber mat to a chemical, solvent, or crosslinker with minimal or no exposure the remainder of the nanofiber mat to the chemical, solvent, or crosslinker.

The methods of the instant invention may further comprise synthesizing the nanofibrous structure (e.g., mat) prior to expansion (e.g., exposure to gas bubbles). In a particular embodiment, the nanofiber mat is synthesized using electrospinning. In a particular embodiment, the nanofiber mat comprises aligned fibers (e.g., uniaxially), random fibers, and/or entangled fibers. The nanofiber mat may be cut or shaped prior to expansion. In a particular embodiment, the nanofiber mat is cut or shaped under cryogenic or frozen conditions (e.g., in liquid nitrogen). The nanofiber mat can be cut or shaped into any desired shape such as, without limitation: rectangles, squares, triangles, quadrangles, pentagons, hexagons, circles, ovals, semicircles, L's, C's, O's, U's, and arches. While the application generally describes nanofiber mats as the 2D structure prior to expansion, the instant invention also encompasses any nanofibrous structure which can be expanded by the methods provided herein (e.g., structures other than a mat or 3D structures which can be further expanded).

In certain embodiments, the nanofiber mat is expanded into an expanded nanofiber structure by exposing the nanofiber mat to gas bubbles. The bubbles can be generated by chemical reactions or physical manipulations. For example, the nanofiber mat can be submerged or immersed in a bubble/gas producing chemical reaction or physical manipulation. Generally, the longer the exposure to the bubbles, the greater the thickness and porosity of the expanded nanofiber structure increases. The nanofiber mat may also be expanded within a mold (e.g., a metal, plastic, or other material that does not expand in the presence of gas bubbles) to assist in the formation of a desired shape. The nanofiber mat may be treated with air plasma prior to exposure to gas bubbles (e.g., to increase hydrophilicity).

After exposure to the bubbles, the expanded nanofiber structure may be washed and/or rinsed in water and/or a desired carrier or buffer (e.g., a pharmaceutically or biologically acceptable carrier). Trapped gas bubbles may be removed by applying a vacuum to the expanded nanofiber structure. For example, the expanded nanofiber structure may be submerged or immersed in a liquid (e.g., water and/or a desired carrier or buffer) and a vacuum may be applied to rapidly remove the gas bubbles. After expansion (e.g., after rinsing and removal of trapped gas), the expanded nanofiber structure may be placed in storage in cold solution or lyophilized and/or freeze-dried.

The gas bubbles of the instant invention can be made by any method known in the art. The bubbles may be generated, for example, by chemical reactions or by physical approaches. Electrospun nanofiber mats can be expanded in the third dimension with ordered structures using gas bubbles generated by chemical reactions in an aqueous solution (see, e.g., WO 2016/053988; WO 2019/060393; Jiang et al. (2018) Acta Biomater., 68:237-248; Jiang, et al. (2015) ACS Biomater. Sci. Eng., 1:991-1001; Jiang, et al. (2016) Adv. Healthcare Mater., 5:2993-3003; Joshi, et al. (2015) Chem. Eng. J., 275:79-88; each of the foregoing incorporated by reference herein). In a particular embodiment, the chemical reaction or physical manipulation does not damage or alter or does not substantially damage or alter the nanofibers (e.g., the nanofibers are inert within the chemical reaction and not chemically modified). As explained hereinabove, the nanofiber mat may be submerged or immersed in a liquid comprising the reagents of the bubble-generating chemical reaction. Examples of chemical reactions that generate bubbles include, without limitation:

$$NaBH_4 + 2H_2O = NaBO_2 + 4H_2$$

$$NaBH_4 + 4H_2O = 4H_2(g) + H_3BO_3 + NaOH$$

$$HCO_3^- + H^+ = CO_2 + H_2O$$

$$NH_4^+ + NO_2^- = N_2 + 2H_2O$$

$$H_2CO_3 = H_2O + CO_2$$

$$2H^+ + S^{2-} = H_2S$$

$$2H_2O_2 = O_2 + 2H_2O$$

$$3HNO_2 = 2NO + HNO_3 + H_2O$$

$$HO_2CCH_2COCH_2CO_2H = 2CO_2 + CH_3COCH_3$$

$$2H_2O_2 = 2H_2 + O_2$$

$$CaC_2 + H_2O = C_2H_2$$

$$Zn + 2HCl = H_2 + ZnCl_2$$

$$2KMnO_4 + 16HCl = 2KCl + 2MnCl_2 + H_2O + 5Cl_2$$

In a particular embodiment, the chemical reaction is the hydrolysis of $NaBH_4$ (e.g., $NaBH_4 + 2H_2O = NaBO_2 + 4H_2$). In a particular embodiment, $CO_2$ gas bubbles (generated chemically or physically) are used (e.g., for hydrophilic polymers).

Examples of physical approaches for generating bubbles of the instant invention include, without limitation: 1) create high pressure (fill gas)/heat in a sealed chamber and suddenly reduce pressure; 2) dissolve gas in liquid/water in high pressure and reduce pressure to release gas bubbles; 3) use supercritical fluids (reduce pressure) like supercritical $CO_2$; 4) use subcritical gas liquid (then reduce pressure) (e.g., liquid $CO_2$, liquid propane and isobutane); 5) fluid flow; 6) apply acoustic energy or ultrasound to liquid/water; 7) apply a laser (e.g., to a liquid or water); 8) boiling; 9) reduce pressure boiling (e.g., with ethanol); and 10) apply radiation (e.g., ionizing radiation on liquid or water). The nanofiber mat may be submerged or immersed in a liquid of the bubble-generating physical manipulation.

In a particular embodiment, the nanofiber mats are expanded using a subcritical or supercritical fluid or liquid (e.g., $CO_2$, $N_2$, $N_2O$, hydrocarbons, and fluorocarbons). In a particular embodiment, liquid $CO_2$ is utilized. For example, nanofiber mats may be expanded by exposing to, contacting with or being placed into (e.g., submerged or immersed) a subcritical liquid/fluid (e.g., subcritical $CO_2$) and then depressurized. The cycle of placing the nanofibrous structures into subcritical $CO_2$ and depressurizing may be performed one or more times. Generally, the more times the expansion method is used the thickness and porosity of the nanofibrous (or microfibrous) structure increases. For examples, the cycle of exposure to subcritical $CO_2$ and then depressurization may be performed one, two, three, four, five, six, seven, eight, nine, ten, or more times, particularly 1-10 times, 1-5 times, or 1-3 times. In a particular embodiment, the cycle of exposure to subcritical $CO_2$ and then depressurization is performed at least 2 times (e.g., 2-10 times, 2-5 times, 2-4 times, or 2-3 times). In a particular embodiment, the method comprises placing the nanofibrous mat and dry ice (solid $CO_2$) in a sealed container, allowing the dry ice to turn into liquid $CO_2$, and then unsealing the container to allow depressurization.

The nanofiber mat and subcritical fluid (e.g., subcritical $CO_2$; or solid form of subcritical fluid (e.g., dry ice)) may be contained in any suitable container (e.g., one which can withstand high pressures). For example, the subcritical fluids and the nanofiber mat may be contained within, but not limited to: chambers, vessels, reactors, chambers, and tubes. In a particular embodiment, the equipment or container used during the methods of the present invention will have a feature or component that allows control of the depressurization rate of the subcritical fluid. Depressurization of the subcritical fluid can be done using a variety of methods including but not limited to manually opening the container to decrease pressure or by using some type of equipment that can regulate the rate of depressurization of the reaction vessel.

The nanofibers of the instant invention may comprise any polymer. In a particular embodiment, the polymer is biocompatible. The polymer may be biodegradable or non-biodegradable. In a particular embodiment, the polymer is a biodegradable polymer. The polymer may by hydrophobic, hydrophilic, or amphiphilic. In a particular embodiment, the polymer is hydrophobic. In a particular embodiment, the polymer is hydrophilic. The polymer may be, for example, a homopolymer, random copolymer, blended polymer, copolymer, or a block copolymer. Block copolymers are most simply defined as conjugates of at least two different polymer segments or blocks. The polymer may be, for example, linear, star-like, graft, branched, dendrimer based, or hyperbranched (e.g., at least two points of branching). The polymer of the invention may have from about 2 to about 10,000, about 2 to about 1000, about 2 to about 500, about 2 to about 250, or about 2 to about 100 repeating units or monomers. The polymers of the instant invention may comprise capping termini Examples of hydrophobic polymers include, without limitation: poly(hydroxyethyl methacrylate), poly(N-isopropyl acrylamide), poly(lactic acid) (PLA (or PDLA)), poly(lactide-co-glycolide) (PLG), poly(lactic-co-glycolic acid) (PLGA), polyglycolide or polyglycolic acid (PGA), polycaprolactone (PCL), poly(aspartic acid), polyoxazolines (e.g., butyl, propyl, pentyl, nonyl, or phenyl poly(2-oxazolines)), polyoxypropylene, poly(glutamic acid), poly(propylene fumarate) (PPF), poly(trimethylene carbonate), polycyanoacrylate, polyurethane, polyorthoesters (POE), polyanhydride, polyester, poly(propylene oxide), poly (caprolactonefumarate), poly(1,2-butylene oxide), poly(n-butylene oxide), poly(ethyleneimine), poly(tetrahydrofurane), ethyl cellulose, polydipyrolle/dicabazole, starch, polyvinylidene fluoride (PVDF), polytetrafluoroethylene (PTFE), polydioxanone (PDO), polyether poly(urethane urea) (PEUU), cellulose acetate, polypropylene (PP), polyethylene terephthalate (PET), nylon (e.g., nylon 6), polycaprolactam, PLA/PCL, poly(3-hydroxybutyrate-co-3-hydroxyvalerate) (PHBV), PCL/calcium carbonate, and/or poly(styrene).

Examples of hydrophilic polymers include, without limitation: polyvinylpyrrolidone (PVP), poly(ethylene glycol) and poly(ethylene oxide) (PEO), chitosan, collagen, chondroitin sulfate, sodium alginate, gelatin, elastin, hyaluronic acid, silk fibroin, sodium alginate/PEO, silk/PEO, silk fibroin/chitosan, hyaluronic acid/gelatin, collagen/chitosan, chondroitin sulfate/collagen, and chitosan/PEO.

Amphiphilic copolymers or polymer composites may comprise a hydrophilic polymer (e.g., segment) and a hydrophobic polymer (e.g., segment) from those listed above (e.g., gelatin/polyvinyl alcohol (PVA), PCL/collagen, chitosan/PVA, gelatin/elastin/PLGA, PDO/elastin, PHBV/collagen, PLA/hyaluronic acid, PLGA/hyaluronic acid, PCL/hyaluronic acid, PCL/collagen/hyaluronic acid, gelatin/siloxane, PLLA/MWNTs/hyaluronic acid).

Examples of polymers particularly useful for electrospinning are provided in Xie et al. (Macromol. Rapid Commun. (2008) 29:1775-1792; incorporated by reference herein; see e.g., Table 1). Examples of compounds or polymers for use in the fibers of the instant invention, particularly for electrospun nanofibers include, without limitation: natural polymers (e.g., chitosan, gelatin, collagen type I, II, and/or III, elastin, hyaluronic acid, cellulose, silk fibroin, phospholipids (Lecithin), fibrinogen, hemoglobin, fibrous calf thymus Na-DNA, virus M13 viruses), synthetic polymers (e.g., PLGA, PLA, PCL, PHBV, PDO, PGA, PLCL, PLLA-DLA, PEUU, cellulose acetate, PEG-b-PLA, EVOH, PVA, PEO, PVP), blended (e.g., PLA/PCL, gelatin/PVA, PCL/gelatin, PCL/collagen, sodium aliginate/PEO, chitosan/PEO, Chitosan/PVA, gelatin/elastin/PLGA, silk/PEO, silk fibroin/chitosan, PDO/elastin, PHBV/collagen, hyaluronic acid/gelatin, collagen/chondroitin sulfate, collagen/chitosan), and composites (e.g., PDLA/HA, PCL/CaCO$_3$, PCL/HA, PLLA/HA, gelatin/HA, PCL/collagen/HA, collagen/HA, gelatin/siloxane, PLLA/MWNTs/HA, PLGA/HA). In a particular embodiment, the nanofiber comprises polymethacrylate, poly vinyl phenol, polyvinylchloride, cellulose, polyvinyl alcohol, polyacrylamide, PLGA, collagen, polycaprolactone, polyurethanes, polyvinyl fluoride, polyamide, silk, nylon, polybennzimidazole, polycarbonate, polyacrylonitrile, polyvinyl alcohol, polylactic acid, polyethylene-co-vinyl acetate, polyethylene oxide, polyaniline, polystyrene, polyvinylcarbazole, polyethylene terephthalate, polyacrylic acid-polypyrene methanol, poly(2-hydroxyethyl methacrylate), polyether imide, polyethylene glycol, poly(ethylene-co-vinyl alcohol), polyacrylnitrile, polyvinyl pyrrolidone, polymetha-phenylene isophthalamide, gelatin, chitosan, starch, pectin, cellulose, methylcellulose, sodium polyacrylate, starch-acrylonitrile co-polymers, and/or combinations of two or more polymers. In a particular embodiment, the polymer comprises polycaprolactone (PCL). In a particular embodiment, the polymer comprises polycaprolactone (PCL) and gelatin (e.g., at a 1:1 ratio).

In a particular embodiment, the nanofiber mat and/or expanded nanofiber structure may further comprise at least one amphiphilic block copolymer comprising hydrophilic poly(ethylene oxide) (PEO) and hydrophobic poly(propylene oxide) (PPO). In a particular embodiment, the nanofiber mat and/or expanded nanofiber structure comprises a poloxamer or an amphiphilic triblock copolymer comprising a central hydrophobic PPO block flanked by two hydrophilic PEO blocks (i.e., an A-B-A triblock structure). In a particular embodiment, the amphiphilic block copolymer is selected from the group consisting of Pluronic® L31, L35, F38, L42, L44, L61, L62, L63, L64, P65, F68, L72, P75, F77, L81, P84, P85, F87, F88, L92, F98, L101, P103, P104, P105, F108, L121, L122, L123, F127, 10R5, 10R8, 12R3, 17R1, 17R4, 17R8, 22R4, 25R1, 25R2, 25R4, 25R5, 25R8, 31R1, 31R2, and 31R4. In a particular embodiment, the nanofiber mat and/or expanded nanofiber structure comprises poloxamer 407 (Pluronic® F127). The amphiphilic block copolymer (e.g., poloxamer) may be added in various amounts to the polymer solution during the synthesis process (e.g., electrospinning). In a particular embodiment, 0% to 20%, particularly 0% to 10%, of the polymer solution is amphiphilic block copolymer (e.g., poloxamer). In a particular embodiment, 0.1% to 5%, particularly 0.5% to 2%, of the polymer solution is amphiphilic block copolymer (e.g., poloxamer). In a particular embodiment, the polymer solution contains 10% polymer (e.g., PCL) and 0.5% poloxamer 407 (Pluronic® F127).

In a particular embodiment, the nanofibers and/or nanofiber structures are coated with additional materials to enhance their properties. For example, the nanofibers and/or nanofiber structure may be coated with proteins, collagen, fibronectin, collagen, a proteoglycans, elastin, or a glycosaminoglycans (e.g., hyaluronic acid, heparin, chondroitin sulfate, or keratan sulfate). In a particular embodiment, the nanofiber structures comprise a material that enhances the nanofiber structure's ability to absorb fluids, particularly aqueous solutions (e.g., blood), and/or allow for the 3D shapes/structures of the expanded nanofiber structure to be recoverable after compression. In a particular embodiment, the nanofibers comprise a polymer and the material which enhances the absorption properties. In a particular embodiment, the nanofibers and/or nanofiber structures are coated with the material which enhances the absorption properties. The term "coat" refers to a layer of a substance/material on the surface of a structure. Coatings may, but need not, also impregnate the nanofiber structure. Further, while a coating may cover 100% of the nanofibers and/or nanofiber structure, a coating may also cover less than 100% of the surface of the nanofibers and/or nanofiber structure (e.g., at least about 75%, at least about 80%, at least about 85%, at least about 90%, at least about 95%, at least about 98%, or more the surface may be coated). Materials which enhance the absorption properties of the expanded nanofiber structures include, without limitation: gelatin, alginate, chitosan, collagen, starch, pectin, cellulose, methylcellulose, sodium polyacrylate, starch-acrylonitrile co-polymers, other natural or synthetic hydrogels, and derivatives thereof (e.g., del Valle et al., Gels (2017) 3:27). In a particular embodiment, the material is a hydrogel (e.g., a polymer matrix able to retain water, particularly large amounts of water, in a swollen state). In a particular embodiment, the material is gelatin. In a particular embodiment, the expanded nanofiber structures are coated with about 0.05% to about 10% coating material (e.g., gelatin), particularly about 0.1% to about 10% coating material (e.g., gelatin) or about 0.1% to about 1% coating material (e.g., gelatin). In a particular embodiment, the material (e.g., hydrogel) is crosslinked In a particular embodiment, the nanofibers and/or nanofiber structures are mineralized (e.g., comprise minerals and/or coated with minerals). Mineralization, for example, with hydroxyapatite, can enhance the adhesion of osteogenic precursor cells in vitro and in vivo (Duan, et al., Biomacromolecules (2017) 18:2080-2089). In a particular embodiment, the nanofibers and/or nanofiber structures are coated with Ca, P, and/or O. In a particular embodiment, the nanofibers and/or nanofiber structures are coated with hydroxyapatite, fluorapatite, and/or chlorapatite, particularly hydroxyapatite. In a particular embodiment, the nanofibers and/or nanofiber structures are immersed in simulated body fluid (SBF) for mineralization (e.g., a solution comprising NaCl, $CaCl_2$, $NaH_2PO_4$, and $NaHCO_3$).

In a particular embodiment, the expanded nanofiber structures of the instant invention have at least one side blocked. For example, a nanofiber mat or membrane may be used to block one or more sides of the expanded nanofiber structure. In a particular embodiment, an aligned nanofiber mat or membrane is used to block one or more sides (e.g., top and bottom) of a radially aligned expanded nanofiber structure.

In a particular embodiment, the nanofiber structures of the instant invention are crosslinked (e.g., before or after expansion). Crosslinking may be done using a variety of techniques including thermal crosslinking, chemical crosslinking, and photo-crosslinking. For example, the nanofiber structures of the instant invention may be crosslinked with a crosslinker such as, without limitation: formaldehyde, paraformaldehyde, acetaldehyde, glutaraldehyde, a photo-crosslinker, genipin, and natural phenolic compounds (Mazaki, et al., Sci. Rep. (2014) 4:4457; Bigi, et al., Biomaterials (2002) 23:4827-4832; Zhang, et al., Biomacromolecules (2010) 11:1125-1132; incorporated herein by reference). The crosslinker may be a bifunctional, trifunctional, or multifunctional crosslinking reagent. In a particular embodiment, the crosslinker is glutaraldehyde.

The expanded nanofiber structures of the instant invention may also comprise holes or wells. The wells/holes may be made in the expanded nanofiber scaffold before or after expansion of the nanofiber mat. In a particular embodiment, the holes of the expanded nanofiber structures are inserted prior to expansion. In a particular embodiment, the nanofiber mat is cryogenic or frozen (e.g., in liquid nitrogen) prior to insertion or punching of the holes. The holes of the nanofiber structure may be any shape (e.g., square, circle). The holes of the expanded nanofiber structure can be any size. In a particular embodiment, the holes/wells have a length/dimension or diameter of about 0.1 to about 5 mm, particularly about 0.5 to about 3 mm or about 1.0 mm. The holes may be organized within the expanded nanofiber structure in an array (e.g., a square array). In a particular embodiment, the holes of the expanded nanofiber structure are generally equidistant from each other. The holes/wells of the expanded nanofiber structures may all be the same size or may be various sizes. Any number of wells may be made in the expanded nanofiber scaffolds. In one embodiment, the number of wells is between about 1 and about 200. The wells may be made using a variety of methods. In one embodiment, a mold with preset holes is used as a template to punch wells/holes into the nanofiber mat and/or expanded nanofiber scaffold. The template may be made using a variety of techniques including but not limited to 3D printing.

The expanded nanofiber structures of the instant invention may also be sterilized. For example, the expanded nanofiber structures can be sterilized using various methods (e.g., by treating with ethylene oxide gas, gamma irradiation, or 70% ethanol).

The expanded nanofiber structure of the instant invention may comprise and/or encapsulate cells or tissue (e.g., within holes/wells of the expanded nanofiber structure, if present). In a particular embodiment, the cells are autologous to the subject to be treated with the nanofiber structure. Any cell type can be added to the expanded nanofiber structure and/or the holes/wells. Cell types include, without limitation: embryonic stem cells, adult stem cells, bone marrow stem cells, induced pluripotent stem cells, progenitor cells (e.g., neural progenitor cells), embryonic like stem cells, mesenchymal stem cells, CAR-T cells, immune cells (including but not limited to T cells, B cells, NK cells, macrophages, neutrophils, dendritic cells and modified forms of these cells and various combinations thereof), cell based vaccines, and cell lines expressing desired therapeutic proteins and/or genes. In a particular embodiment, the cells comprise stem cells. In a particular embodiment, the cells comprise dermal fibroblasts. In a particular embodiment, the cells are cell spheroids. In a particular embodiment, the expanded nanofiber structure and/or the holes/wells comprise tissue samples (e.g., minced tissue), such as skin tissue samples or bone samples. In a particular embodiment, the tissue samples have a length/dimension of diameter of about 0.1 to about 5 mm, particularly about 0.5 to about 3 mm or about 1.0 mm. The cells or tissue may be cultured with in the holes/wells of the nanofiber structure (e.g., the cells or tissue may be cultured for sufficient time to allow for infiltration into the nanofiber structure). For example, the cells or tissue may be cultured in the expanded nanofiber structure for 1 day, 2 days, 3 days, 4 days, 5 days, or more.

The expanded nanofiber structures of the instant invention may comprise or encapsulate at least one agent, particularly a bioactive agent such as a biologic, drug or therapeutic agent (e.g., analgesic, growth factor, anti-inflammatory, signaling molecule, cytokine, antimicrobial (e.g., antibacterial, antibiotic, antiviral, and/or antifungal), blood clotting agent, factor, or protein, etc.). In a particular embodiment, the agent is hydrophilic. The agent may be added to the nanofiber structures during synthesis and/or after synthesis. The agent may be conjugated to the nanofiber structure and/or coating material, encapsulated by the nanofiber structure, and/or coated on the nanofiber structure (e.g., with, underneath, and/or on top of the coating that enhances the nanofiber structure's ability to absorb fluids). In a particular embodiment, the agent is not directly conjugated to the nanofiber structure (e.g., encapsulated). In a particular embodiment, the agent is conjugated or linked to the nanofiber structure (e.g., surface conjugation or coating). In a particular embodiment, the agents are administered with but not incorporated into the expanded nanofiber structures.

Biologics include but are not limited to proteins, peptides, antibodies, antibody fragments, DNA, RNA, and other known biologic substances, particularly those that have therapeutic use. In a particular embodiment, the agent is a drug or therapeutic agent (e.g., a small molecule) (e.g., analgesic, growth factor, anti-inflammatory, signaling molecule, cytokine, antimicrobial (e.g., antibacterial, antibiotic, antiviral, and/or antifungal), blood clotting agent, factor, or protein, pain medications (e.g., anesthetics), etc.). In a particular embodiment, the agent enhances tissue regeneration, tissue growth, and wound healing (e.g., growth factors). In a particular embodiment, the agent treats/prevents infections (e.g., antimicrobials such as antibacterials, antivirals and/or antifungals). In a particular embodiment, the agent is an antimicrobial, particularly an antibacterial. In a particular embodiment, the agent enhances wound healing and/or enhances tissue regeneration (e.g., bone, tendon, cartilage, skin, nerve, and/or blood vessel). Such agents include, for example, growth factors, cytokines, chemokines, immunomodulating compounds, and small molecules. Growth factors include, without limitation: platelet derived growth factors (PDGF), vascular endothelial growth factors (VEGF), epidermal growth factors (EGF), fibroblast growth factors (FGF; e.g., basic fibroblast growth factor (bFGF)), insulin-like growth factors (IGF-1 and/or IGF-2), bone morphogenetic proteins (e.g., BMP-2, BMP-7, BMP-12, BMP-9; particularly BMP-2 fragments, peptides, and/or analogs thereof), transforming growth factors (e.g., TGFβ, TGFβ3), nerve growth factors (NGF), neurotrophic factors, stromal derived factor-1 (SDF-1), granulocyte-macrophage colony-stimulating factor (GM-CSF), granulocyte-colony stimulating factor (G-CSF), erythropoietin (EPO), glial cell-derived neurotrophic factors (GDNF), hepatocyte growth factors (HGF), keratinocyte growth factors (KGF), and/or growth factor mimicking peptides (e.g., VEGF mimicking peptides). Chemokines include, without limitation: CCL21, CCL22, CCL2, CCL3, CCL5, CCL7, CCL8, CCL13, CCL17, CXCL9, CXCL10, and CXCL11. Cytokines include without limitation IL-2 subfamily cytokines, interferon subfamily cytokines, IL-10 subfamily cytokines, IL-1, I-18, IL-17, tumor necrosis factor, and transforming-growth factor beta superfamily cytokines. Examples of small molecule drugs/therapeutic agents include, without limitation, simvastatin, kartogenin, retinoic acid, paclitaxel, vitamins (e.g., vitamin D3), etc. In a particular embodiment, the agent is a blood clotting factor such as thrombin or fibrinogen. In a particular embodiment, the agent is a bone morphogenetic protein (e.g., BMP-2, BMP-7, BMP-12, BMP-9; particularly human; particularly BMP-2 fragments, peptides, and/or analogs thereof). In a particular embodiment, the agent is a BMP-2 peptide such as KIPKASSVPTELSAISTLYL (SEQ ID NO: 1). In a particular embodiment, the agent is a BMP-2 fragment (e.g., up to about 25, about 30, about 35, about 40, about 45, about 50 amino acids, or more of BMP-2) comprising the knuckle epitope (e.g., amino acids 73-92 of BMP-2 or SEQ ID NO: 1). In a particular embodiment, the BMP-2 peptide is linked to a peptide of acidic amino acids (e.g., Asp and/or Glu; particularly about 3-10 or 5-10 amino acids such as E7, E8, D7, D8) and/or bisphosphonate (e.g., at the N-terminus).

In a particular embodiment, the agents enhance tissue regeneration, tissue growth, and wound healing (e.g., growth factors). In a particular embodiment, the agent treats/prevents infections (e.g., antimicrobials such as antibacterials, antivirals and/or antifungals). In a particular embodiment, the agent is an antimicrobial, particularly an antibacterial. In a particular embodiment, the agent enhances wound healing and/or enhances tissue regeneration (e.g., bone, tendon, cartilage, skin, nerve, and/or blood vessel). Such agents include, for example, growth factors, cytokines, chemokines, immunomodulating compounds, and small molecules. Growth factors include, without limitation: platelet derived growth factor (PDGF), vascular endothelial growth factor (VEGF), epidermal growth factor (EGF), fibroblast growth factor (FGF, multiple isotypes; e.g. basic fibroblast growth factor (bFGF)), insulin-like growth factor (IGF-1 and/or IGF-2), bone morphogenetic protein (e.g., BMP-2, BMP-7, BMP-12, BMP-9), transforming growth factor (e.g., TGFβ, TGFβ3), nerve growth factor (NGF), neurotrophic factor, stromal derived factor-1 (SDF-1), glial cell-derived neurotrophic factor (GDNF), and/or keratinocyte growth factor (KGF). Small molecules include, without limitation, simvastatin, kartogenin, retinoic acid, paclitaxel, vitamin D3, etc.

The instant application also encompasses the expanded nanofiber structures synthesized by the methods of the instant invention. Compositions comprising the expanded nanofiber structures synthesized by the methods of the instant invention and at least one pharmaceutically or biologically acceptable carrier are also encompassed by the instant invention.

The expanded nanofiber structures of the instant invention can be used to create complex tissue architectures for a variety of application including, without limitation: wound healing, tissue engineering, tissue growth, tissue repair, tissue regeneration, and engineering 3D in vitro tissue models. Applications for nanofibrous structures are provided in Xie et al. (Macromol. Rapid Commun. (2008) 29:1775-1792; incorporated by reference herein). Some examples of potential uses for the 3D nanofibrous structures of the present invention include but are not limited to use as tissue scaffolds (in vitro or in vivo), hemostatic bandages, tissue repair scaffolds, and tissue regeneration scaffolds. The expanded nanofiber structures can also be combined with a variety of hydrogels or biological matrices/cues to form 3D hybrid scaffolds that can release biologically functional molecules. The tissue constructs can be used for regeneration of many tissue defects (e.g., skin, bone) and healing of various wounds (e.g., injuries, diabetic wounds, venous ulcer, pressure ulcer, burns). The expanded nanofiber structures may be used ex vivo to generate tissue or tissue constructs/models. The expanded nanofiber structures may also be used in vivo in patients (e.g., human or animal) for the treatment of various diseases, disorders, and wounds. In a particular embodiment, the nanofiber structure stimulates the growth of existing tissue and/or repair of a wound or defect (e.g., bone defect) when applied in vivo. The expanded nanofiber scaffolds can be used for engineering, growing, and/or regeneration of a variety of tissues including but not limited to skin, bone, cartilage, muscle, nervous tissue, and organs (or portions thereof).

In accordance with the instant invention, the expanded nanofiber structures may be used in inducing and/or improving/enhancing wound healing and inducing and/or improving/enhancing tissue regeneration. The expanded nanofiber structures of the present invention can be used for the treatment, inhibition, and/or prevention of any injury or wound. For example, the expanded nanofiber structures can be used to induce, improve, or enhance wound healing associated with surgery (including non-elective (e.g., emergency) surgical procedures or elective surgical procedures). Elective surgical procedures include, without limitation: liver resection, partial nephrectomy, cholecystectomy, vascular suture line reinforcement and neurosurgical procedures. Non-elective surgical procedures include, without limitation: severe epistaxis, splenic injury, liver fracture, cavitary wounds, minor cuts, punctures, gunshot wounds, and shrapnel wounds. The expanded nanofiber structures of the present invention can also be incorporated into delivery devices (e.g., a syringe) that allow for their injection/delivery directly into a desired location (e.g., a wound such as a gunshot wound). The expanded nanofiber structures also may be delivered directly into a cavity (such as the peritoneal cavity) using a pressurized cannula.

In accordance with the instant invention, methods for inducing and/or improving/enhancing wound healing in a subject are also provided. Methods of inducing and/or improving/enhancing tissue regeneration (e.g., blood vessel growth, neural tissue regeneration, and bone regeneration) in a subject are also encompassed by the instant invention. The methods of the instant invention comprise administering or applying an expanded nanofiber structure of the instant invention to the subject (e.g., at or in a wound). The expanded nanofibers of the instant invention may be compressed prior to administration to the subject. In a particular embodiment, the method comprises administering an expanded nanofiber structure comprising an agent as described hereinabove. In a particular embodiment, the method comprises administering an expanded nanofiber structure to the subject and an agent as described hereinabove (i.e., the agent is not contained within the nanofiber structure). When administered separately, the expanded nanofiber structure may be administered simultaneously and/or sequentially with the agent. The methods may comprise the administration of one or more nanofiber structures. When more than one expanded nanofiber structure is administered, the expanded nanofiber structures may be administered simultaneously and/or sequentially.

In a particular embodiment of the instant invention, methods for modulating (increasing) hemostasis; inhibiting blood loss; and/or treating hemorrhage are provided. In a particular embodiment, the method comprises administering the expanded nanofiber structure to the wound or site of bleeding. In a particular embodiment, the expanded nanofiber structure comprises a blood clotting factor such as thrombin and/or fibrinogen.

In a particular embodiment of the instant invention, methods for stimulating bone regeneration and/or treating bone loss are provided. In a particular embodiment, the method comprises administering the expanded nanofiber structure to the site of bone loss. In a particular embodiment, the site of bone loss is periodontal. In a particular embodiment, the expanded nanofiber structure is mineralized. In a particular embodiment, the expanded nanofiber structure comprises a bone growth stimulating growth factor such as a bone morphogenic protein or fragment or analog thereof. In a particular embodiment, the agent is a bone morphogenetic protein (e.g., BMP-2, BMP-7, BMP-12, BMP-9; particularly human; particularly BMP-2 fragments, peptides, and/or analogs thereof). In a particular embodiment, the agent is a BMP-2 peptide such as KIPKASSVPTELSAIST-LYL (SEQ ID NO: 1). In a particular embodiment, the agent is a BMP-2 fragment (e.g., up to about 25, about 30, about 35, about 40, about 45, about 50 amino acids, or more of BMP-2) comprising the knuckle epitope (e.g., amino acids 73-92 of BMP-2 or SEQ ID NO: 1). In a particular embodiment, the BMP-2 peptide is linked to a peptide of acidic amino acids (e.g., Asp and/or Glu; particularly about 3-10 or 5-10 amino acids such as E7, E8, D7, D8) and/or bisphosphonate (e.g., at the N-terminus).

In accordance with the instant invention, the expanded nanofiber structures of the present invention can be used to treat and/or prevent a variety of diseases and disorders. Examples of diseases and/or disorders include but are not limited to wounds, ulcers, infections, hemorrhage, tissue injury, tissue defects, tissue damage, bone fractures, bone degeneration, cancer (e.g., the use of docetaxel and curcumin for the treatment of colorectal cancer (Fan, et al., Sci. Rep. (2016) 6:28373)), neurologic diseases (e.g., Alzheimer's and Parkinson's), ischemic diseases, inflammatory diseases and disorders, heart disease, myocardial infarction, and stroke.

The expanded nanofiber structures can also be used to expand and increase cell numbers (e.g., stem cell numbers) in culture. In a particular embodiment, microtissues can be grown in situ by prolonged culture of a cell laden expanded nanofiber structure. These expanded nanofiber structures are transplantable into a tissue defect to promote wound healing in a subject (e.g., the expanded nanofiber structure comprise autologous cells).

Definitions

The singular forms "a," "an," and "the" include plural referents unless the context clearly dictates otherwise.

As used herein, the term "electrospinning" refers to the production of fibers (i.e., electrospun fibers), particularly micro- or nano-sized fibers, from a solution or melt using interactions between fluid dynamics and charged surfaces (e.g., by streaming a solution or melt through an orifice in response to an electric field). Forms of electrospun nanofibers include, without limitation, branched nanofibers, tubes, ribbons and split nanofibers, nanofiber yarns, surface-coated nanofibers (e.g., with carbon, metals, etc.), nanofibers produced in a vacuum, and the like. The production of electrospun fibers is described, for example, in Gibson et al. (1999) AIChE J., 45:190-195.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., TrisHCl, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E.W. Martin (Mack Publishing Co., Easton, PA); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients (3rd Ed.), American Pharmaceutical Association, Washington.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

"Hydrophobic" designates a preference for apolar environments (e.g., a hydrophobic substance or moiety is more readily dissolved in or wetted by non-polar solvents, such as hydrocarbons, than by water). In a particular embodiment, hydrophobic polymers may have aqueous solubility less than about 1% wt. at 37° C. In a particular embodiment, polymers that at 1% solution in bi-distilled water have a cloud point below about 37° C., particularly below about 34° C., may be considered hydrophobic.

As used herein, the term "hydrophilic" means the ability to dissolve in water. In a particular embodiment, polymers that at 1% solution in bi-distilled water have a cloud point above about 37° C., particularly above about 40° C., may be considered hydrophilic.

As used herein, the term "amphiphilic" means the ability to dissolve in both water and lipids/apolar environments. Typically, an amphiphilic compound comprises a hydrophilic portion and a hydrophobic portion.

The term "antimicrobials" as used herein indicates a substance that kills or inhibits the growth of microorganisms such as bacteria, fungi, viruses, or protozoans.

As used herein, the term "antiviral" refers to a substance that destroys a virus and/or suppresses replication (reproduction) of the virus. For example, an antiviral may inhibit and or prevent: production of viral particles, maturation of viral particles, viral attachment, viral uptake into cells, viral assembly, viral release/budding, viral integration, etc.

As used herein, the term "antibiotic" refers to antibacterial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, an "anti-inflammatory agent" refers to compounds for the treatment or inhibition of inflammation. Anti-inflammatory agents include, without limitation, non-steroidal anti-inflammatory drugs (NSAIDs; e.g., aspirin, ibuprofen, naproxen, methyl salicylate, diflunisal, indomethacin, sulindac, diclofenac, ketoprofen, ketorolac, carprofen, fenoprofen, mefenamic acid, piroxicam, meloxicam, methotrexate, celecoxib, valdecoxib, parecoxib, etoricoxib, and nimesulide), corticosteroids (e.g., prednisone, betamethasone, budesonide, cortisone, dexamethasone, hydrocortisone, methylprednisolone, prednisolone, tramcinolone, and fluticasone), rapamycin, acetaminophen, glucocorticoids, steroids, beta-agonists, anticholinergic agents, methyl xanthines, gold injections (e.g., sodium aurothiomalate), sulphasalazine, and dapsone.

As used herein, the term "subject" refers to an animal, particularly a mammal, particularly a human.

As used herein, the term "prevent" refers to the prophylactic treatment of a subject who is at risk of developing a condition resulting in a decrease in the probability that the subject will develop the condition.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "analgesic" refers to an agent that lessens, alleviates, reduces, relieves, or extinguishes pain in an area of a subject's body (i.e., an analgesic has the ability to reduce or eliminate pain and/or the perception of pain).

As used herein, the term "small molecule" refers to a substance or compound that has a relatively low molecular weight (e.g., less than 2,000). Typically, small molecules are organic, but are not proteins, polypeptides, or nucleic acids.

The term "hydrogel" refers to a water-swellable, insoluble polymeric matrix (e.g., hydrophilic polymers) comprising a network of macromolecules, optionally crosslinked, that can absorb water to form a gel.

The term "crosslink" refers to a bond or chain of atoms attached between and linking two different molecules (e.g., polymer chains). The term "crosslinker" refers to a molecule capable of forming a covalent linkage between compounds. A "photocrosslinker" refers to a molecule capable of forming a covalent linkage between compounds after photoinduction (e.g., exposure to electromagnetic radiation in the visible and near-visible range). Crosslinkers are well known in the art (e.g., formaldehyde, paraformaldehyde, acetaldehyde, glutaraldehyde, etc.). The crosslinker may be a bifunctional, trifunctional, or multifunctional crosslinking reagent.

The following examples illustrate certain embodiments of the invention. They are not intended to limit the invention in any way.

Example 1

In mathematics, a solid of revolution is a solid figure obtained by rotating a plane curve around some straight line (the axis of revolution) that lies on the same plane. Based on the concept of solids of revolution, a 3D object can be built by rotating an area around a predetermined center line called the axis of rotation. Based on the same concept, people used the potter's wheel (or potter's lathe) for producing works of art several thousand years ago (Rous, et al. (2009) Levant 41:155-173). 2D nanofiber mats can be expanded using a gas-foaming technique along the fiber deposition direction with well-controlled thickness and porosity (Jiang, et al. (2015) ACS Biomater. Sci. Eng., 1:991-1001; Jiang, et al. (2016) Adv. Healthc. Mater., 5:2993-2003; Jiang, et al. (2018) Acta Biomater., 68:237-248; Woodruff, et al. (2010) Prog. Polym. Sci., 35:1217-1256). Herein, it was determined whether a 2D nanofiber membrane could transform into a 3D predesigned complex shape if one side of the 2D membrane was fixed during the expansion process.

Materials and Methods

Materials

PCL (Mw=80 kDa), Pluronic®-F127, gelatin, sodium borohydride, Triton X-100 were purchased from Sigma-Aldrich (St. Louis, MO). Dichloromethane (DCM) and N,N-dimethylformamide (DMF) were purchased from BDH Chemicals (Dawsonville, GA). Dulbecco's modified eagle medium (DMEM), fetal bovine serum (FBS), and penicillin-streptomycin, fibroblast growth factor (FGF), Laminin, B27 and neurobasal medium were obtained from Invitrogen (Carlsbad, CA). Tuj 1 primary antibody and Goat anti-mouse IgG H&L (Alexa Fluor® 647) secondary antibody was purchased from Abcam (Cambridge, MA).

Fabrication of 2D Electrospun Nanofiber Mats

Electrospun PCL nanofiber mats were fabricated. Two grams PCL beads and 0.1 g Pluronic®-F127 were dissolved in 20 ml DCM and DMF mixed solvent at a ratio of 4:1 (v/v), the final concentration of PCL is 10% and the final concentration of Pluronic®-F127 is 0.5%. After PCL/Pluronic®-F127 solution was transparent, 50 ml PCL/F-127 solution was pumped at a flow rate of 0.7 ml/h using a syringe pump while a potential of 18 kV was applied between the spinneret (22 Gauge needle) and a grounded collector. Around 1 mm thick aligned PCL nanofiber mat was collected by a high-speed rotating drum.

Fabrication of 3D Predesigned Complex Shapes

The 2D nanofiber mats were cut into different shapes in the liquid nitrogen, including rectangle (5 mm×1.5 mm or 10 mm×5 mm), right triangle (10 mm×5 mm), semicircle (diameter 10 mm), and arch (external diameter 10 mm, inner diameter 6 mm) nanofiber mats. Then, one side of these PCL nanofiber mats was fixed by thermo treatment (85° C. for 1 second). Subsequently, these PCL nanofiber mats with one side fixed were immersed in 1 M NaBH$_4$ solution which was gently shaken for 30 minutes. After expansion, the transformed shapes were transferred into the distilled water and exposed to a vacuum (~200 Pa) for 10 seconds. This process was repeated for 3 times. Finally, the distilled water was removed, and the 3D shapes were exposed to a vacuum until it froze and then freeze dried.

Alternatively, the 3D shapes can be obtained by depressurization of subcritical $CO_2$ fluid as well. The 2D PCL nanofiber mat was cut into rectangle mats (5 mm×2 mm) along with the fiber alignment direction. Then one side was fixed by thermal treatment (85° C. for 1 second). About 1 g of dry ice and one piece of nanofiber mat with one side fixed were put into a 30 mL Oak Ridge centrifuge tube at room temperature. After the dry ice changed into $CO_2$ fluid, the cap was rapidly loosened and the 3D nanofiber shape was obtained and recorded by a digital camera. The aforementioned process was then repeated until it was fully expanded.

Characterization of Predesigned Complex 3D Shapes

The photographs of complex 3D shapes were recorded by a digital camera. In order to enhance the mechanical property of the transformed 3D shapes, they were immersed in 0.5% gelatin solution for 10 minutes. The residual gelatin solution was then removed. Subsequently, these 3D shapes were exposed to a vacuum until it froze and then freeze dried. No crosslinking was performed for the gelatin coating. Such a coating was used to enhance its mechanical property and maintain its integrity during the frozen section process. After the section, the gelatin coating can be removed by washing. To enhance the mechanical property, the gelatin coating was cross-linked using glutaraldehyde. The cross sections of 3D shapes (X-Y, Y-Z, X-Z planes) were characterized by SEM (FEI, Quanta 200, Oregon, USA).

The porosity of nanofiber shapes was calculated according to the volume difference between the estimated bulk materials and expanded nanofiber shapes. Porosity was estimated based on the following equation:

$$\varepsilon = (V - V_0)/V \times 100\%$$

where $\varepsilon$ is porosity, $V = \int_a^b A(x)dx$ or $\int_a^b (A_1(x) - A_2(x))dx$ is the volume of a nanofiber shape or a hollow nanofiber shape, $V_0 = m_0/\rho_0$ is the calculated volume of bulk PCL material, $m_0$ is the mass of bulk PCL material, and $\rho_0$ is the density of bulk PCL materials. Based on this equation, the calculated porosity of nanofiber cylinders was $(98.87 \pm 0.63)\%$.

Fibroblast Culture on 3D Shapes

In order to demonstrate the cell culture throughout the shapes, 3D shapes made of radially aligned nanofibers were fabricated and sterilized with ethylene oxide for 12 hours. Green fluorescent protein (GFP)-labeled fibroblasts suspension with a concentration of $1 \times 10^7$ cell/ml were first prepared. 3D shapes were put into the cell suspension solution and treated with vacuum for 10 seconds. Then, these 3D shapes were removed from the cell solution and placed into 0.1% agar pretreated 24-well plate. One ml DMEM medium plus with 10% FBS, 1% penicillin-streptomycin was added and the medium was changed every two days. At each indicated time point, the 3D shape was collected and washed with PBS for 3 times. Then, the 3D shapes were fixed with 4% paraformaldehyde for 15 minutes and washed with PBS for 3 times. Finally, the distribution and growth of fibroblast in the 3D shapes was characterized by confocal laser scanning microscopy (Zeiss, Oberkochen, Germany).

Rat Neural Progenitor Cell Culture

The rat neural progenitor cells were cultured in laminin precoated 10-cm culture dish with maintenance medium, DMEM/F12 medium plus with 20 ng/ml FGF, and 1 µg/ml laminin After reaching 80% confluence, cells were digested and the cell density was adjusted to $1 \times 10^7$ cells/ml. Then, 1 ml cell suspension solution was dropped to each nanofiber cylinder consisting of radially-aligned PCL nanofibers, and cultured for 48 hours. These cells were differentiated with neurobasal medium plus with 0.5% B27 for 5 days and 14 days respectively. At each indicated time point, the cells-seeded nanofiber cylinders consisting of radially-aligned PCL nanofibers were fixed with 4% paraformaldehyde.

Immunofluorescence Staining

The fixed, rat neural progenitor cells-seeded nanofiber cylinders consisting of radially-aligned PCL nanofibers were washed with PBS for 3 times, 5 minutes for each time. Then, the seeded cells were permeabilized with 0.1% Triton X-100 for 20 minutes, washed with PBS for 3 times, 5 minutes for each time. Next, the seeded cells were blocked with 5% bovine serum albumin (BSA) for 30 minutes. After this, the seeded cells were incubated with Tuj 1 (1:100) primary antibody overnight and washed with PBS for 3 times, 5 minutes for each time, then following by incubation with goat anti-mouse IgG H&L (Alexa Fluor® 647) secondary antibody (1:200) for 1 hour and washing with PBS for 3 times, 5 minutes for each time. Finally, Tuj 1 positive cells were imaged by confocal laser scanning microscopy (Zeiss, Oberkochen, Germany).

Subcutaneous Implantation

Briefly, the rats were anesthetized using 4% isoflurane in oxygen for approximately 2 minutes. Rats were placed on a heating pad to maintain their body temperature and continuously anesthetized by 2% isoflurane during surgery. An area of $4 \times 4$ $cm^2$ on the back of each animal was shaved, and povidone-iodine solution was applied three times on the exposed skin. Subcutaneous pockets were made (1 cm incisions) on both side of dorsum, each implant (diameter: 10 mm; height: 1.5 mm) was directly inserted into a subcutaneous pocket by tweezers and the skin incisions were closed with a stapler, totally each mouse received 2 implants. Three rats were considered as a treatment group to investigate, totally 6 implants for each group. Rats were euthanized by $CO_2$ at 1, 2, 4 and 8 weeks post-implantation. Each explant with surrounding tissue was gently dissected out of its subcutaneous pocket, and then immersed in formalin for at least 3 days prior to histology analysis.

Histology

Fixed samples were dehydrated in a graded ethanol series (70%-100%), embedded in paraffin, and then sectioned (5 µm). Samples were performed with either hematoxyline and eosin (H & E) or masson's trichrome staining according to standard procedures.

Results

Poly($\varepsilon$-caprolactone) (PCL), a Food Drug Administration (FDA) approved, biodegradable, and biocompatible polymers for specific applications used in the human body, was used as raw material. 1 mm thick 2D nanofiber mats were fabricated using a rotating mandrel as a collector during electrospinning as described (Jiang, et al. (2015) ACS Biomater. Sci. Eng., 1:991-1001; Jiang, et al. (2016) Adv. Healthc. Mater., 5:2993-2003; Jiang, et al. (2018) Acta Biomater., 68:237-248; Woodruff, et al. (2010) Prog. Polym. Sci., 35:1217-1256). The fiber mat was then cut in liquid nitrogen with different 2D shapes (e.g., rectangle, half circle, arch, and triangle). Thermal treatment was then used to fix one side of 2D nanofiber membranes. Subsequently, the 2D membranes were expanded in a $NaBH_4$ solution (Jiang, et al. (2015) ACS Biomater. Sci. Eng., 1:991-1001; Jiang, et al. (2016) Adv. Healthc. Mater., 5:2993-2003). It was expected that the 2D rectangle membrane would transform into a predesigned 3D complex shape (e.g., cylinder). The transformation process is illustrated in FIG. 1A.

Figure 1B:
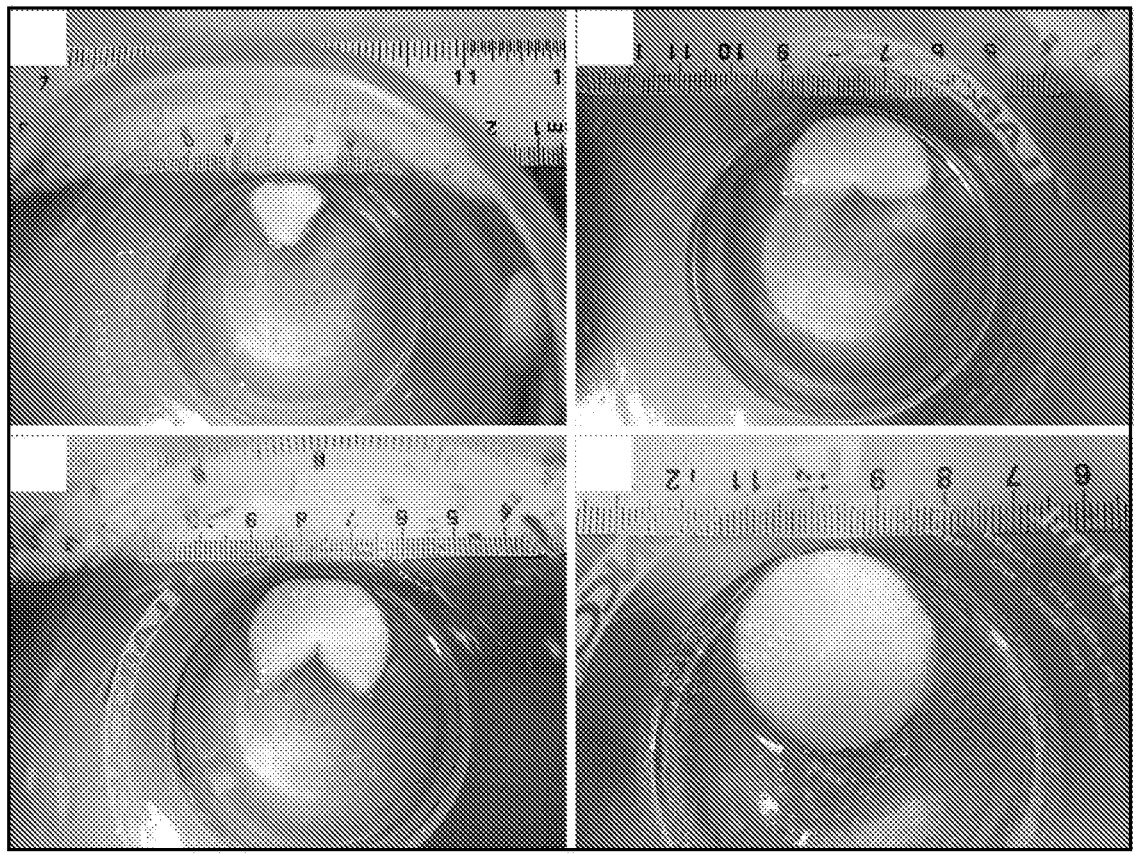
FIG. 1B provides images of different shapes generated at different expansion times: 30 minutes (top left), 60 minutes (top right), 90 minutes (bottom left), and 135 minutes (bottom right).
Figure 1C:
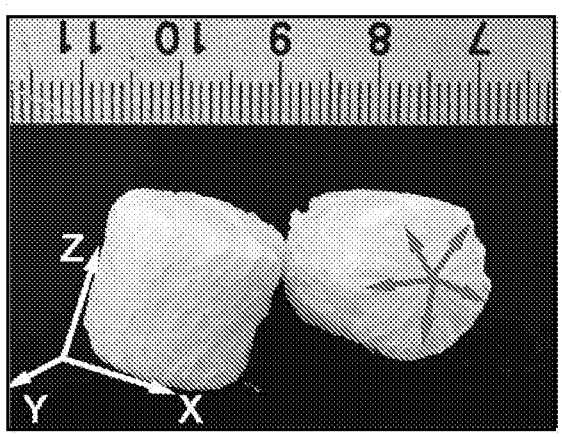
FIG. 1C provides a photograph of transformed cylinders.
Figure 1D:
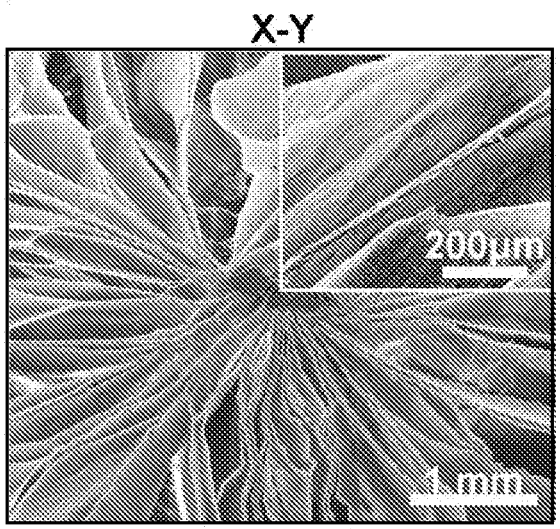
FIG. 1D provides a scanning electron microscopy (SEM) image showing the X-Y plan made of the radially aligned nanofibers and the porous structure of X-Y plane.
Figure 1E:
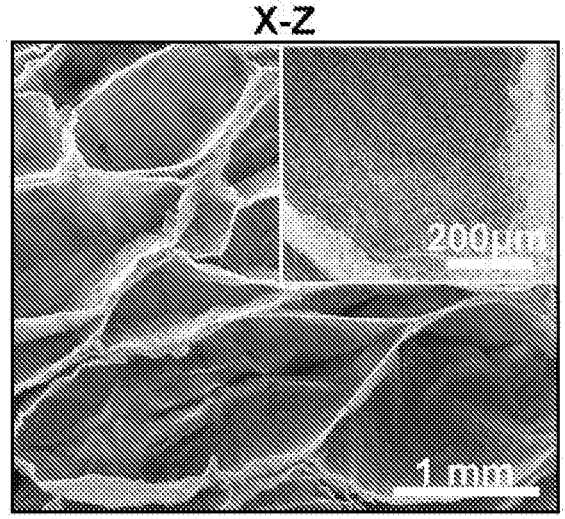
FIG. 1E provides a SEM image showing the porous structure of the X-Z plane.
Figure 1F:
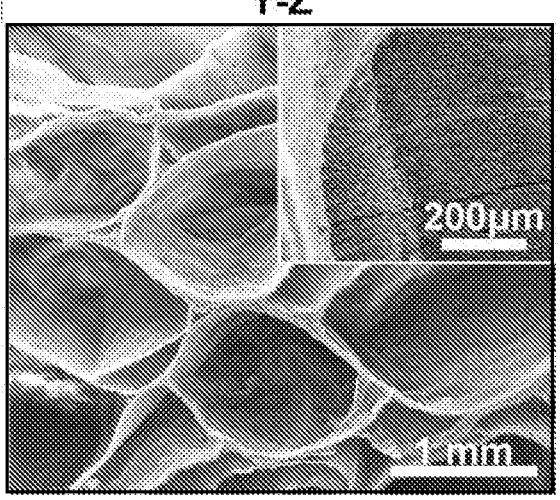
FIG. 1F provides a SEM image showing the porous structure of the Y-Z plane. The fiber alignment is along the X-axis. Arrows indicate the direction of fiber alignment.

At different expansion times, it was observed that a fan shape was formed at 30 minutes followed by a half cylinder formed at 60 minutes, a three-quarter cylinder formed at 90 minutes, and a cylinder formed at 135 minutes (FIG. 1B). Therefore, it is possible to obtain different shapes by freeze-drying the samples at different times of expansion. Alternatively, a negative pressure was applied through a lyophilizer to speed up the expansion process (i.e., shorten the expansion time) after an initial expansion in the NaBH$_4$ aqueous solution. FIG. 1C shows a photograph of cylinders transformed from 2D rectangle nanofiber mats after freeze-drying. The cylinders were further characterized using scanning electron microscopy (SEM). The cylinders were made of numerous nanofiber thin films/layers (FIG. 1D). The X-Y plane of transformed nanofiber cylinders was made of radially-aligned nanofibers and the X-Z and Y-Z planes showed a highly porous structure (FIGS. 1D-1F). The nanofiber layers were ~15 μm thick. The width of gaps between layers in cylinders ranged from several microns to hundreds of microns, which could be tailored by varying the initial thickness of 2D nanofiber mats.

Figure 2A:
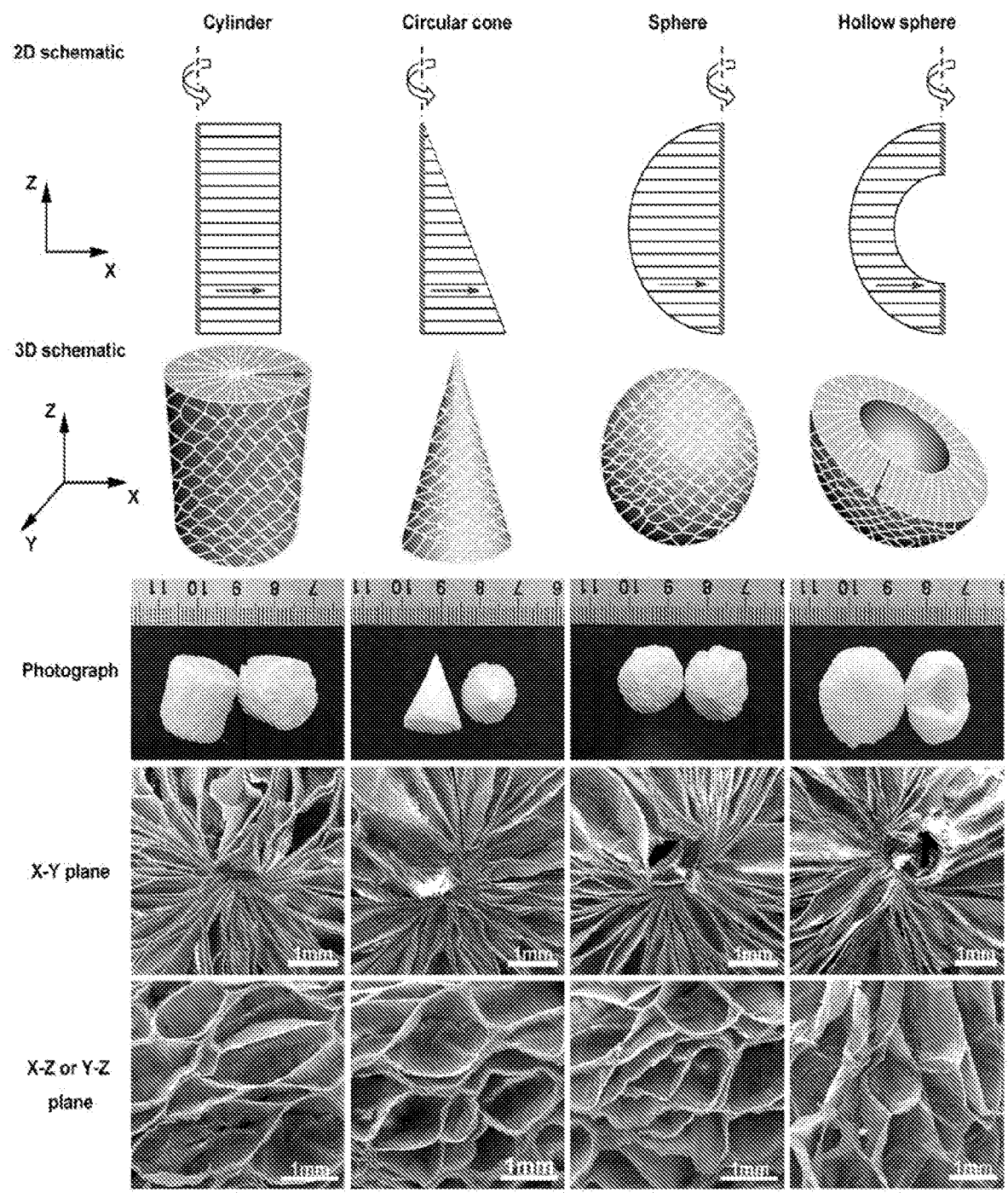
FIG. 2A shows the transformation of 2D rectangle, triangle, semicircle, and arch nanofiber mats into cylinders, circular cones, spheres, and hollow spheres. The fiber alignment is along the X-axis direction. Photographs and SEM images are also provided.
Figure 2B:
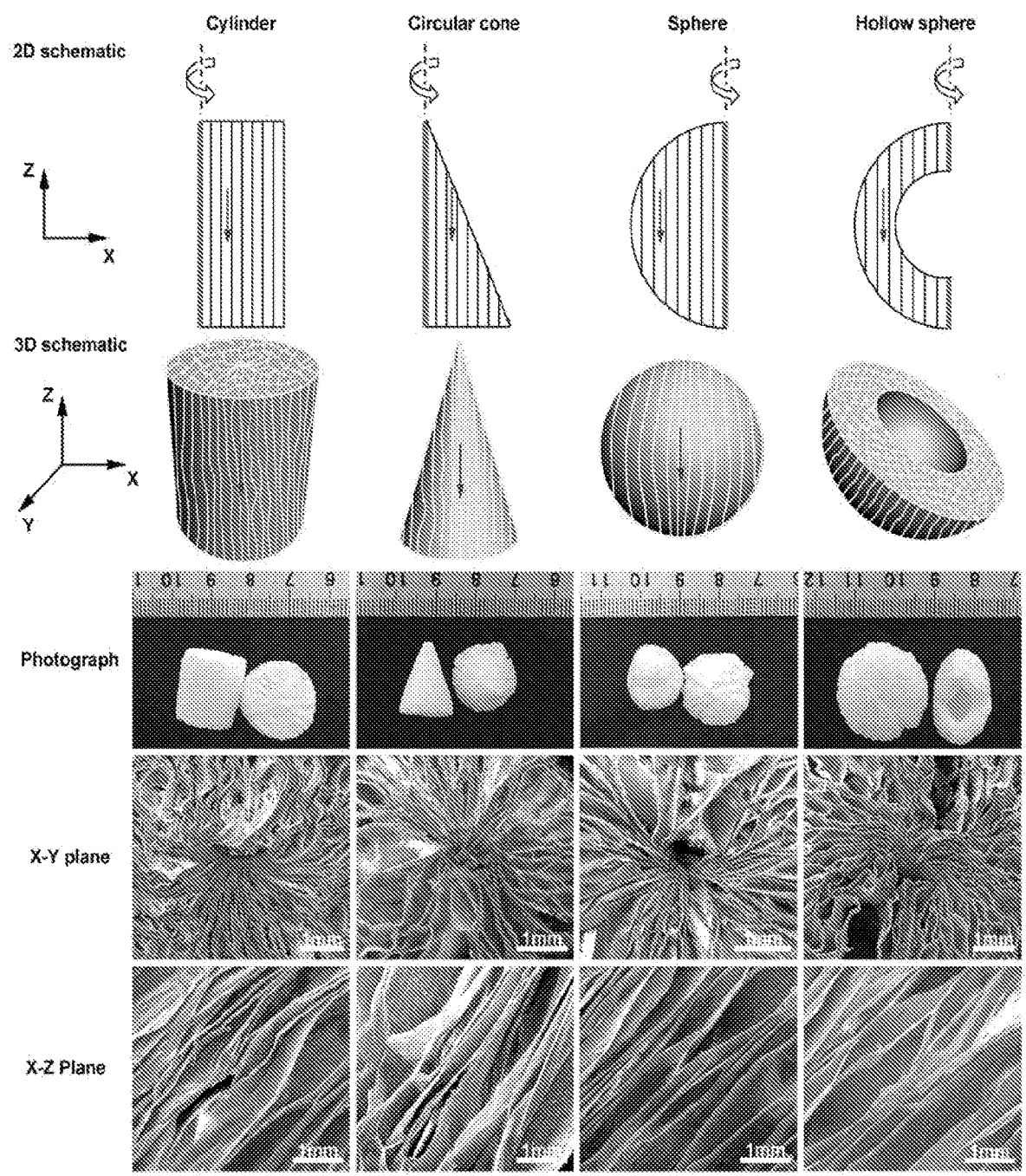
FIG. 2B shows the transformation of 2D rectangle, triangle, semicircle, and arch nanofiber mats into cylinders, circular cones, spheres, and hollow spheres. The fiber alignment is along the Z-axis direction. Photographs and SEM images are also provided.
Figure 2C:
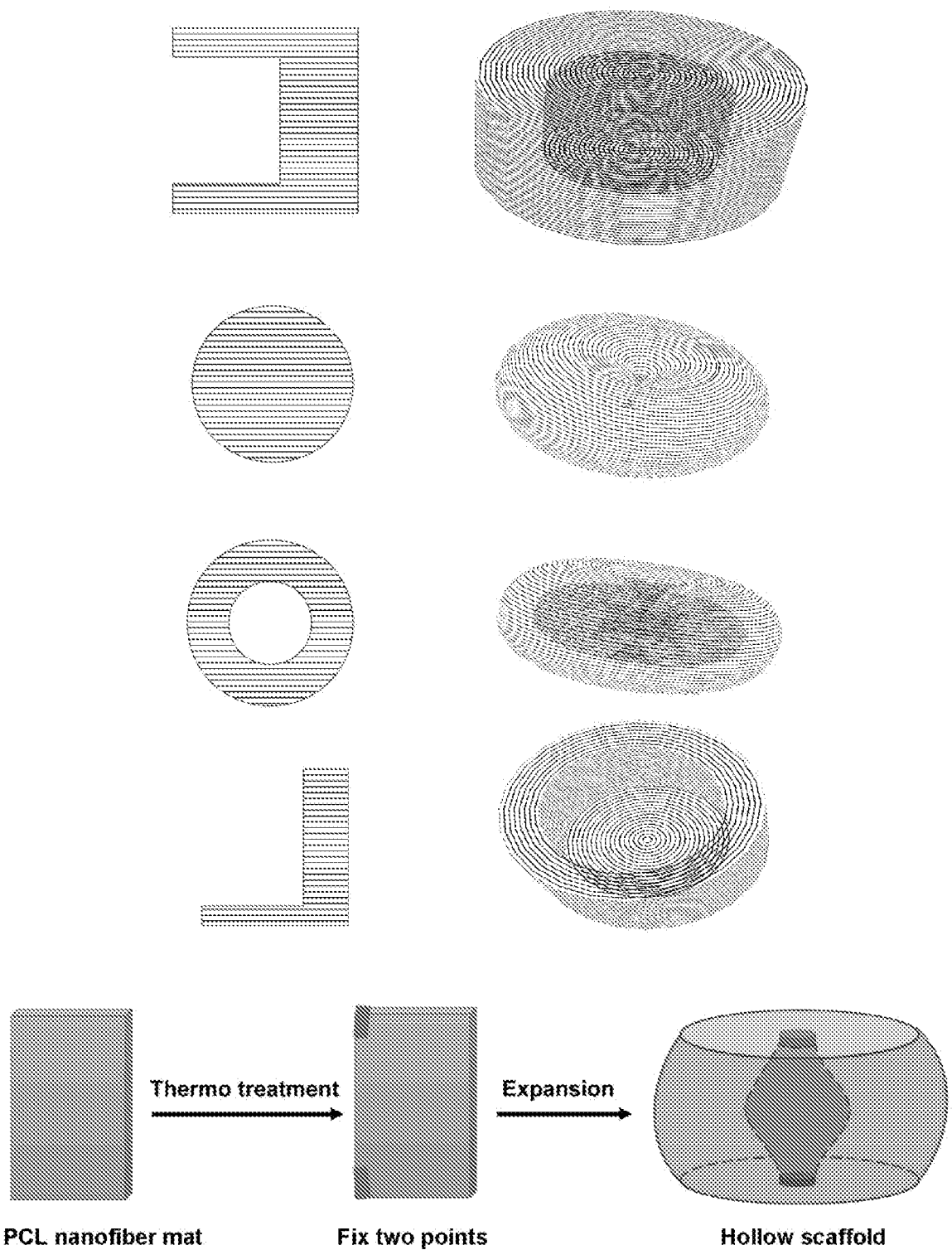
FIG. 2C provides schematics of other shapes that can be fabricated.

Based on the same principle, the 2D triangle, semicircle, and arch nanofiber membranes were successfully transformed into predesigned 3D complex shapes including circular cones, spheres, and hollow spheres (FIG. 2A). Additionally, a different direction of fiber alignment in transformed complex shapes can be readily realized as one can switch to another side for thermal fixation (FIG. 2B). In this case, the cylinders were made of nanofibers with alignment along the Z-axis, which could be useful to mimic the structures of tissues with anisotropic properties such as tendon, muscle, and nerve (Kannus, P. (2000) Scand J. Med. Sci. Sports, 10:312-320; Frontera, et al. (2015) Calcif. Tissue Int., 96:183-195; Xie, et al. (2010) Nanoscale 2:35-44). Similarly, other shapes including circular cones, spheres, and hollow spheres can be fabricated using the same strategy (FIG. 2B). FIG. 2C provides schematics of other shapes which can be synthesized using this strategy.

Figure 3A:
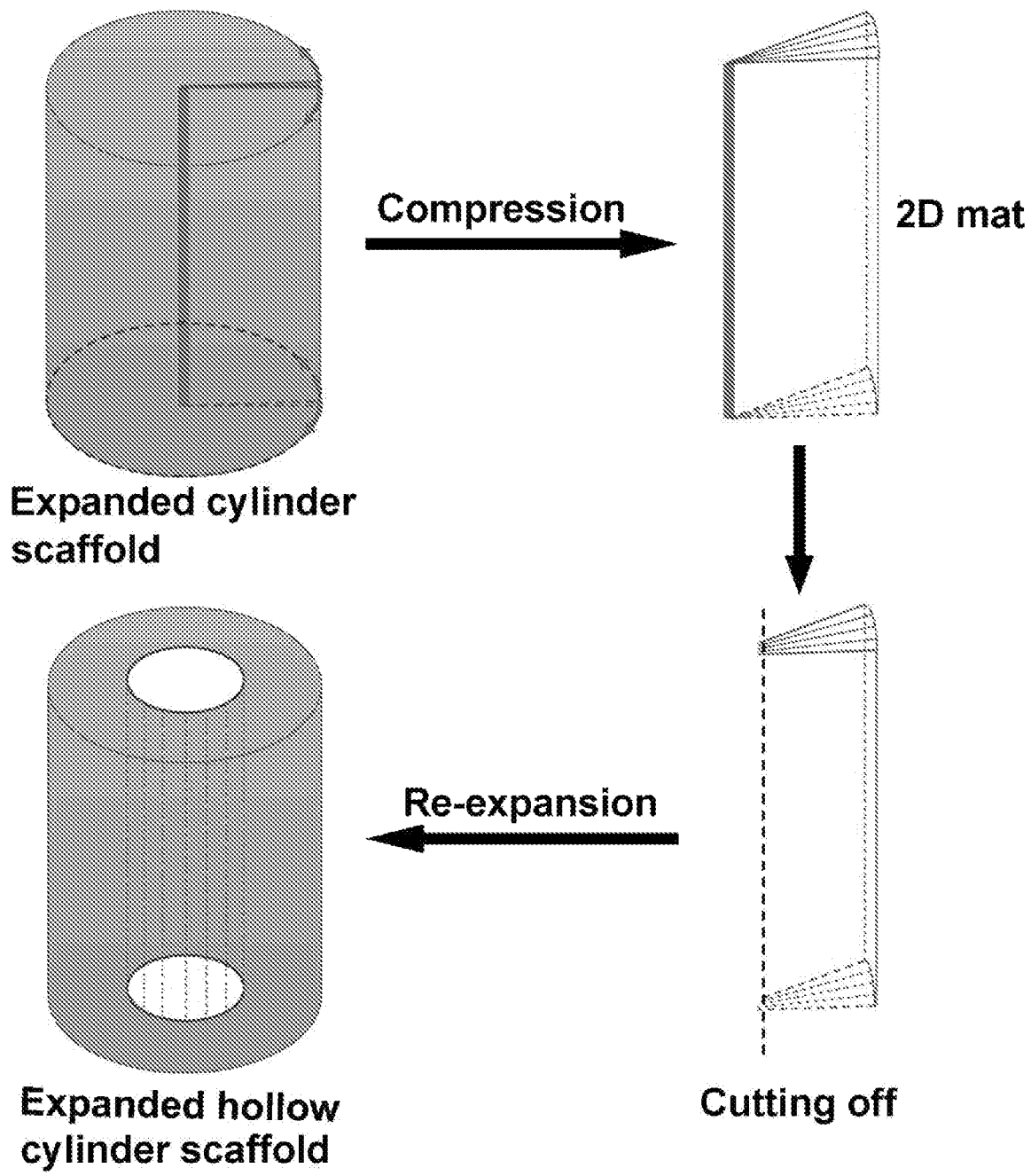
FIG. 3A provides a schematic illustrating the fabrication of hollow cylinders (thick line indicates fixed side). The cylinders are compressed to 2D mats and then certain areas (labeled in dash line) are cut the mat is re-expanded to form hollow cylinders.
Figure 3B:
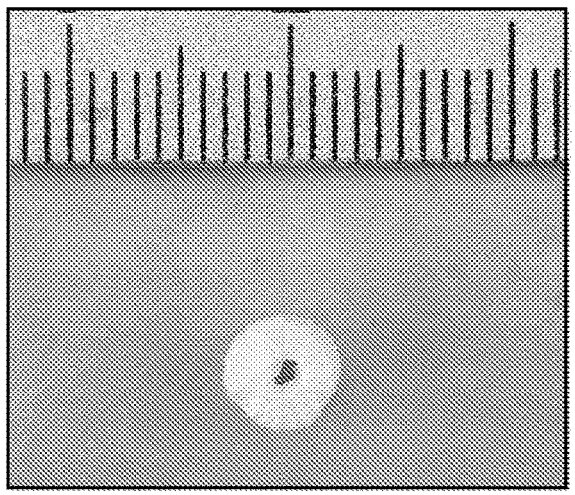
FIG. 3B provides a photograph of a hollow cylinder.
Figure 3C:
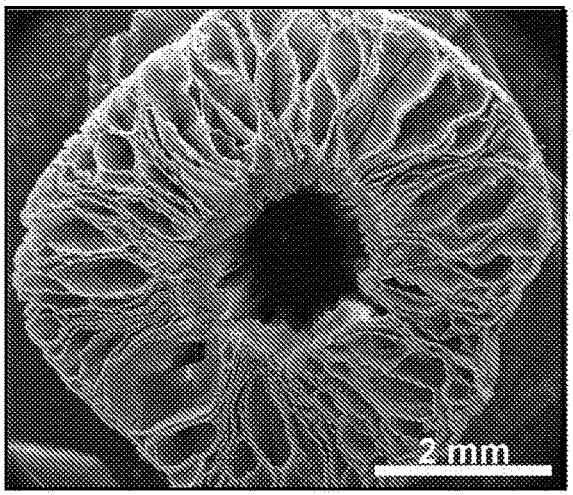
FIG. 3C-3E provide SEM images of a hollow cylinder with different magnifications. Fibers were aligned along the longitudinal direction of the tubes.
Figure 3D:
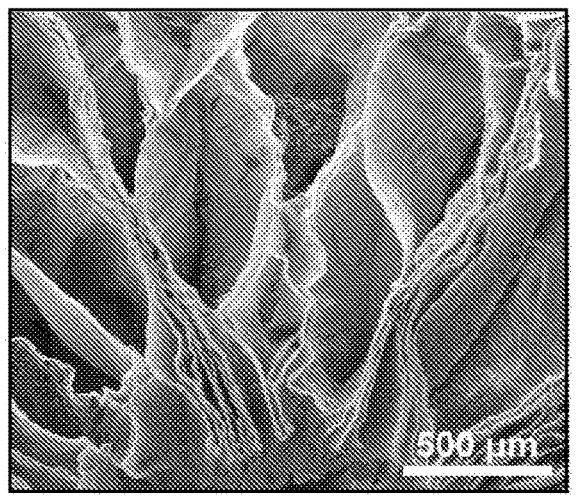
Figure 3E:
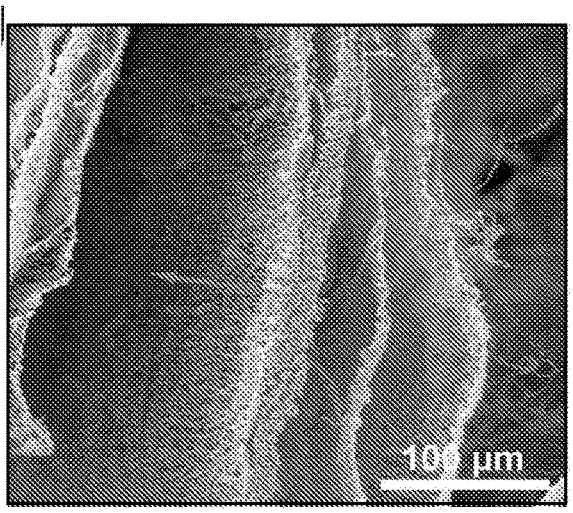

Tubular-structured tissues/organs are omnipresent throughout the human body, normally found in the vasculature (e.g., arteries, veins, capillaries), respiratory (e.g., trachea, esophagus), urinary (e.g., ureter, urethra, bladder), and gastrointestinal systems (Holland, et al. (2018) Bio-Design and Manufacturing 1:89-100). Tissue engineering of these tubular organs are of the great interest due to a number of surgeries performed annually on those organs (Gora, et al. (2016) J. Nanosci. Nanotechnol., 16:19-39). Towards this end, tubular nanofiber scaffolds (hollow cylinders) were fabricated based on the cylinders transformed from 2D nanofiber mats. FIG. 3A illustrates the fabrication of hollow cylinders. Briefly, the cylinders were compressed to a 2D mat and the area along the fixed side was cut. Then, the compressed and sliced mats were re-expanded to form hollow cylinders. FIG. 3B shows a photograph of a hollow cylinder. FIG. 3C shows a SEM image of the cross section of the hollow cylinder, indicating a highly porous, layered structure. It is seen that the gaps between layers were in the range of tens of microns to hundreds of microns (FIG. 3E). Similarly, the thickness for each layer was around ~15 μm (FIG. 3D). By varying the alignment of fibers in the 2D mats, hollow cylinders consisting of aligned fibers either in the radial direction or in the longitudinal direction can be readily generated, which could be useful to mimic the smooth muscle structures in the tubular tissues.

Figure 4:
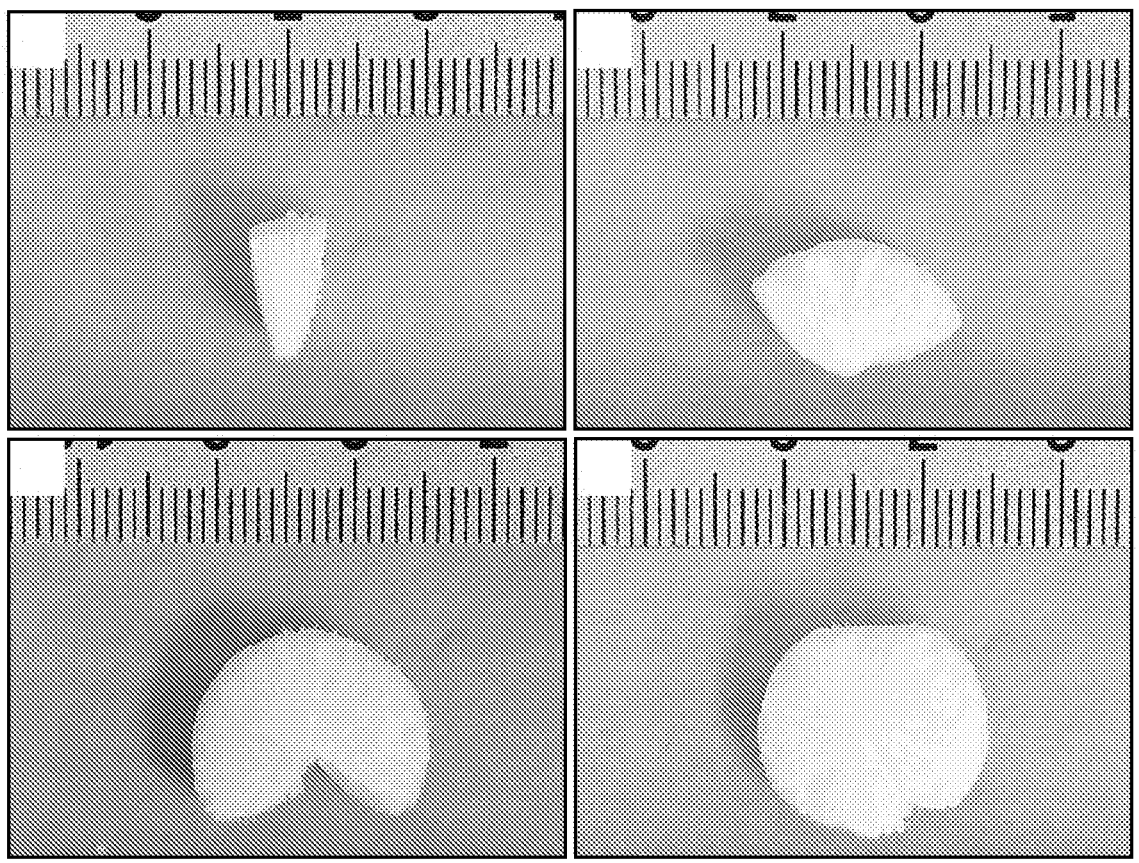
FIG. 4 provides photographs showing various complex shapes. The shapes were transformed from 2D mats through depressurization of subcritical $CO_2$ fluid for different times: once (top left), twice (top right), three times (bottom left), and four times (bottom right).

2D nanofiber mats can be expanded in the third dimension with ordered structures using gas bubbles generated by chemical reactions in an aqueous solution (Jiang, et al. (2015) ACS Biomater. Sci. Eng., 1:991-1001; Jiang, et al. (2016) Adv. Healthc. Mater. 5:2993-2003). However, this method was associated with a number of limitations: multistep, time-consuming, involving an aqueous solution, necessity of freeze-drying, possible reactions between NaBH$_4$ and polymers or encapsulated substances, loss of bioactive materials encapsulated in fibers, possible loss of bioactivities for biomacromolecules incorporated in the fibers, and not suitable for water-soluble materials. $CO_2$ expanded 3D nanofiber scaffolds can eliminate many of the issues listed above and better maintain the activity of encapsulated bioactive materials compared to previous approaches due to the low-temperature process (Jiang, et al. (2018) Acta Biomater., 68:237-248). Therefore, 2D nanofiber mats were transformed to 3D predesigned complex shapes through depressurization of subcritical $CO_2$ fluid. To demonstrate the proof-of-concept, 2D rectangle nanofiber mat with one fixed side was depressurized in subcritical $CO_2$ fluid following our recent studies. Intriguingly, different 3D shapes can be obtained after depressurization of subcritical $CO_2$ for different expansion times (FIG. 4). Similar to the expansion in the NaBH$_4$ solution for 30 minutes, fan shapes were formed after depressurization of subcritical $CO_2$ for once and twice (FIG. 4). A three quarter cylinder was formed after depressurization for three times (FIG. 4). A cylinder was formed after $CO_2$ treatment for four times (FIG. 4).

Gelatin-coated, expanded nanofiber matrices show super-elastic and shape-recovery properties in air and liquid (Chen, et al. (2018) Biomaterials 179:46-59). Based on the similar principle, gelatin-coated nanofiber cylinders could almost recover to their original shape (>95%) after first compression and placed into water. Interestingly, the coated nanofiber cylinders could recover more than 75% after the fourth compression. By reducing pressure, 100% shape recovery can readily be achieved in water. Such shape-recoverable property allows the developed nanofiber shapes used in the minimally invasive surgery. For example, the nanofiber scaffold can be compressed for insertion and, optionally, the shape can be recovered by administration of water or saline.

Figure 5A:
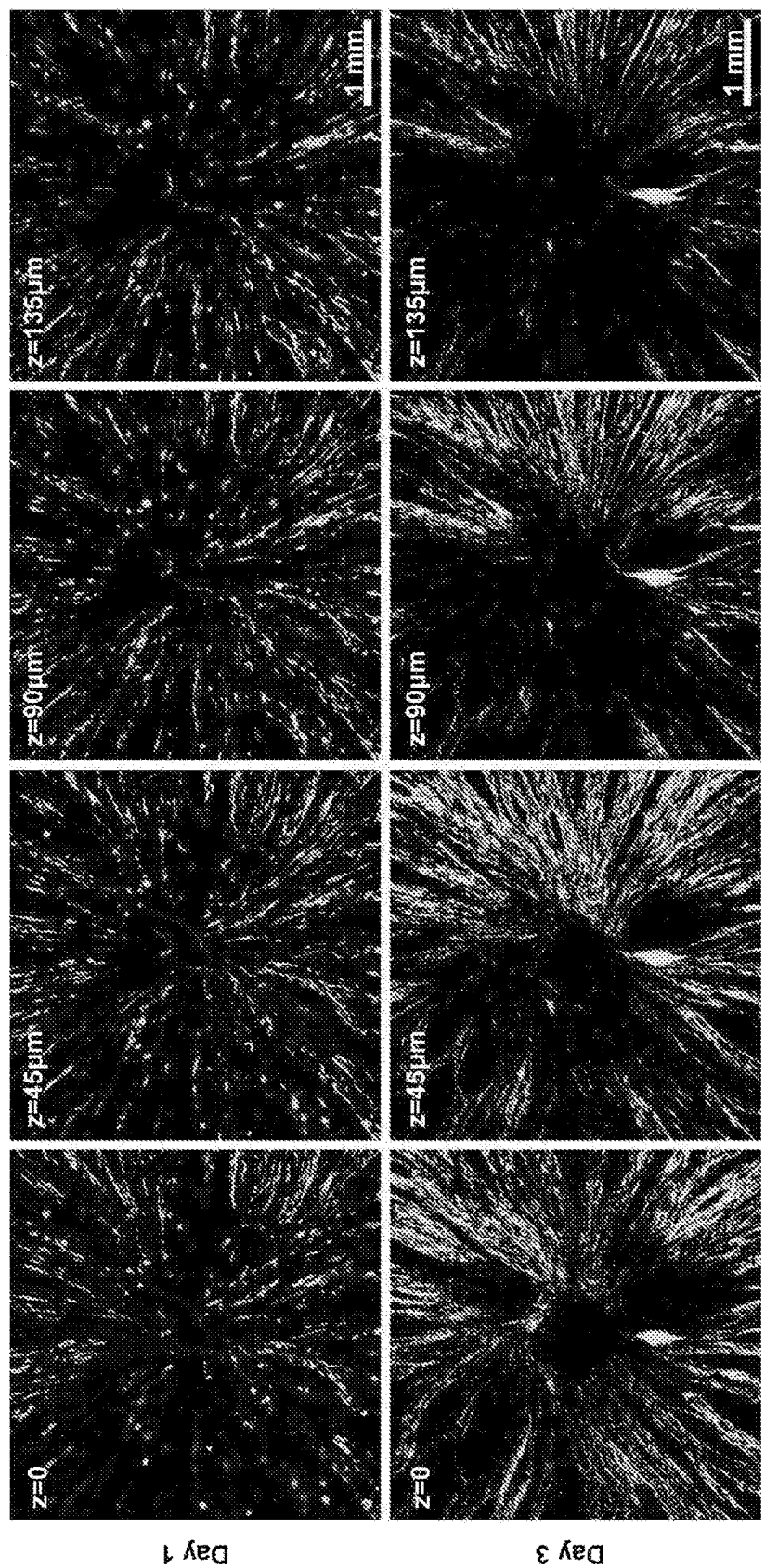
FIGS. 5A and 5B provide images of GFP-labeled dermal fibroblast culture on expanded, radially-aligned and vertically-aligned PCL nanofiber scaffolds.
Figure 5B:
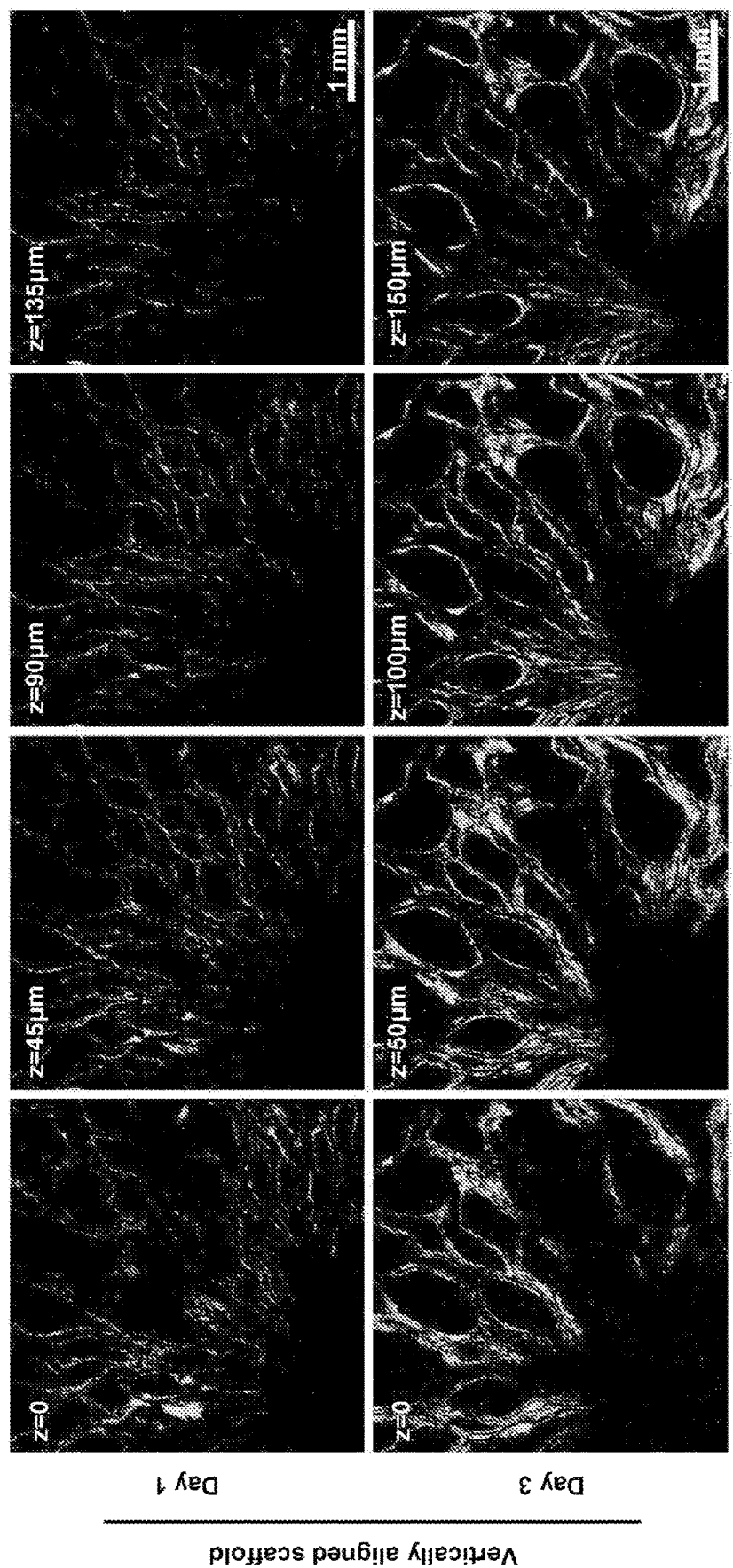
Figure 5C:
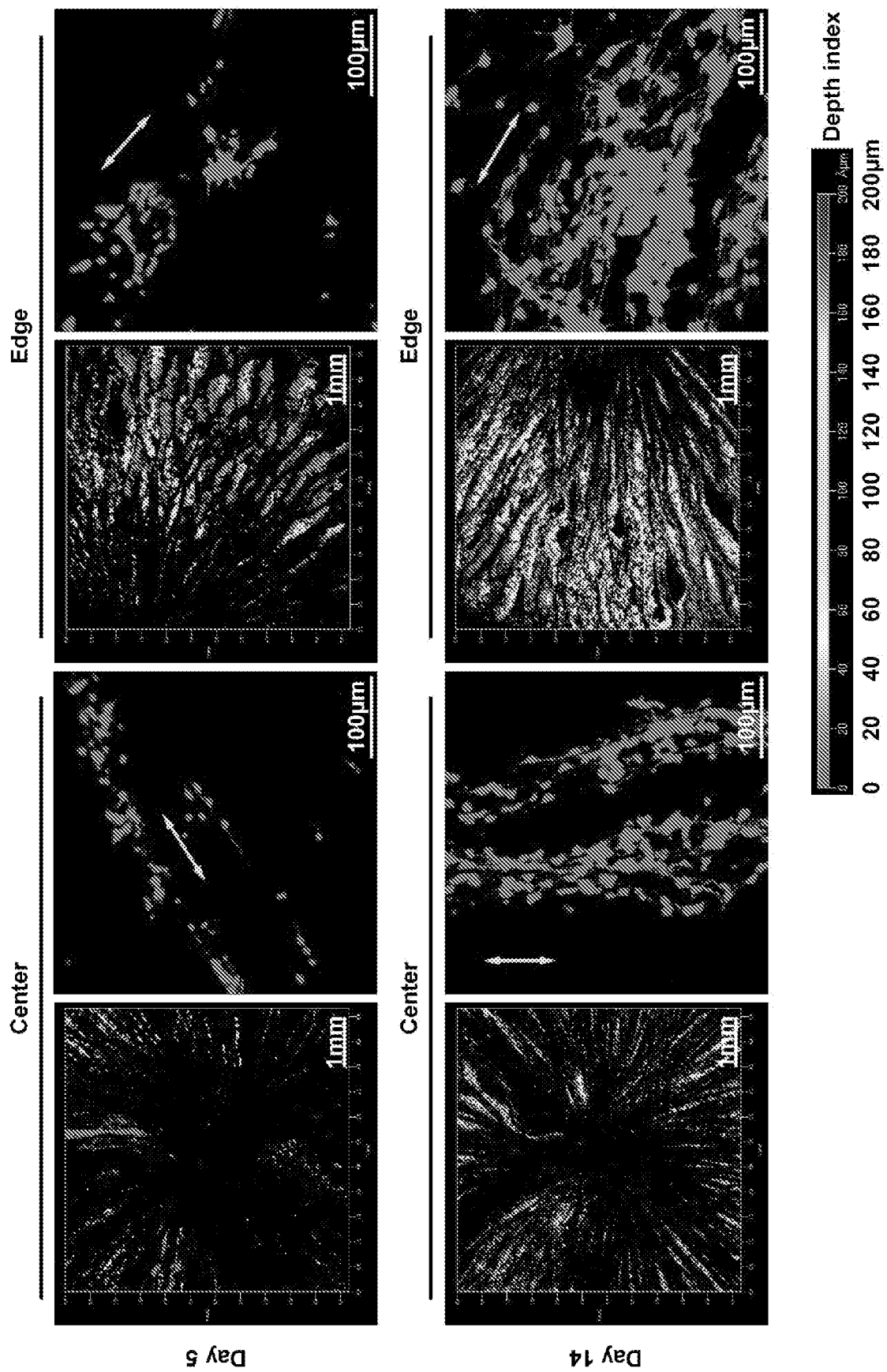
FIG. 5C provides images of rat neural progenitor cell culture on expanded, radially-aligned PCL nanofiber scaffolds. The distribution of rat neural progenitor cells in the center and on the edge of 1-mm-thickness expanded, radially-aligned PCL nanofiber scaffolds after culturing for 5 or 14 days (left), and immunohistochemistry staining with Tuj 1 marker indicates differentiated neurons with neurite outgrowth (right). Double-headed arrows indicate the fiber alignment direction.

Studies have shown that aligned nanofibers can provide contact guidance for various types of cells (Xie, et al. (2010) ACS Nano 4:5027-5036; Chew, et al. (2008) Biomaterials 29:653-661; Xie, et al. (2014) ACS Nano 8:1878-1885; Kubow, et al. (2017) Sci. Rep., 7:14380). 3D shapes composed of aligned nanofiber thin films could guide organization of seeded and proliferated cells to form highly ordered 3D tissue constructs. To demonstrate this, green fluorescent protein (GFP)-labeled dermal fibroblasts were seeded to the transformed cylinders (diameter: 10 mm; height: 1.5 mm) in which the X-Y plane was made of radially-aligned nanofibers and vertically-aligned nanofibers. FIG. 5 shows the GFP-labeled dermal fibroblasts seeded on cylinders for 1 day and 3 days. Due to the limited thickness that confocal microscopy can image, the cells within the cylinder from top surface to 135 and 150 μm deep were imaged and shown in FIG. 5. It is seen that cells distributed uniformly throughout the imaged thickness of cylinder. In addition, the seeded and proliferated cells displayed radially-aligned patterns in each scanning layer emulating the X-Y plane structure of nanofiber cylinders (FIG. 5A), while dermal fibroblasts formed alignment along the longitudinal direction of cylinders consisting of vertically aligned nanofibers (FIG. 5B). It was further demonstrated the rat neural progenitor cell culture on the cylindrical shapes consisting of radially-aligned nanofibers. Neural precursor cells were evenly distributed throughout the shapes and able to proliferate and differentiate into neurons, exhibiting an organized structure (FIG. 5C). The neurites were displayed in a radial fashion emulating the fiber alignment of the shapes. Such 3D ordered neural tissue constructs could be used for building in vitro 3D neural tissue models and repairing nerve injuries.

Direct deposition of radially-aligned 2D nanofiber membranes on a special collector made of a ring electrode and a point electrode located at the center during electrospinning (Xie, et al. (2010) ACS Nano 4:5027-5036; Li, et al. (2016)

Small 12:5009-5018). This 2D membrane showed the promotion of cell migration from the surrounding area to the center. However, this method is restricted to the generation of 2D nanofiber membranes with limited thickness. The current work overcomes this limitation by generating radially-aligned nanofiber scaffolds/devices with predesigned thickness and porosity. Such nanofiber cylinders could be used for in situ tissue regeneration and wound healing, as the radially-aligned nanofibers are capable of directing and promoting cell migration from the surrounding host tissues. In addition, it is believed that cells could penetrate the cylinders through the surrounding sides, and top and bottom surfaces, indicated an advantage compared to expanded 3D nanofiber scaffolds previously developed as the cells were mainly infiltrated from the surrounding sides (Jiang, et al. (2015) ACS Biomater. Sci. Eng., 1:991-1001; Jiang, et al. (2016) Adv. Healthc. Mater., 5:2993-2003; Jiang, et al. (2018) Acta Biomater., 68:237-248).

Figure 6B:
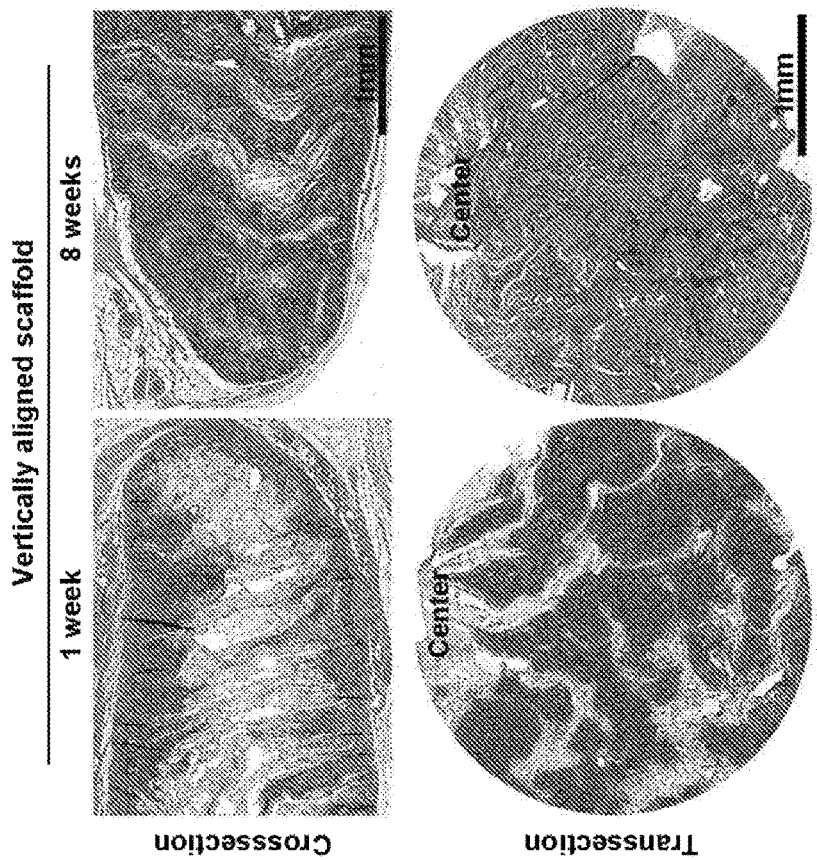
FIGS. 6A-6D show in vivo response of expanded, radially-aligned and vertically-aligned PCL nanofiber scaffolds after subcutaneous implantation for 1 and 8 weeks in rats.
Figure 6A:
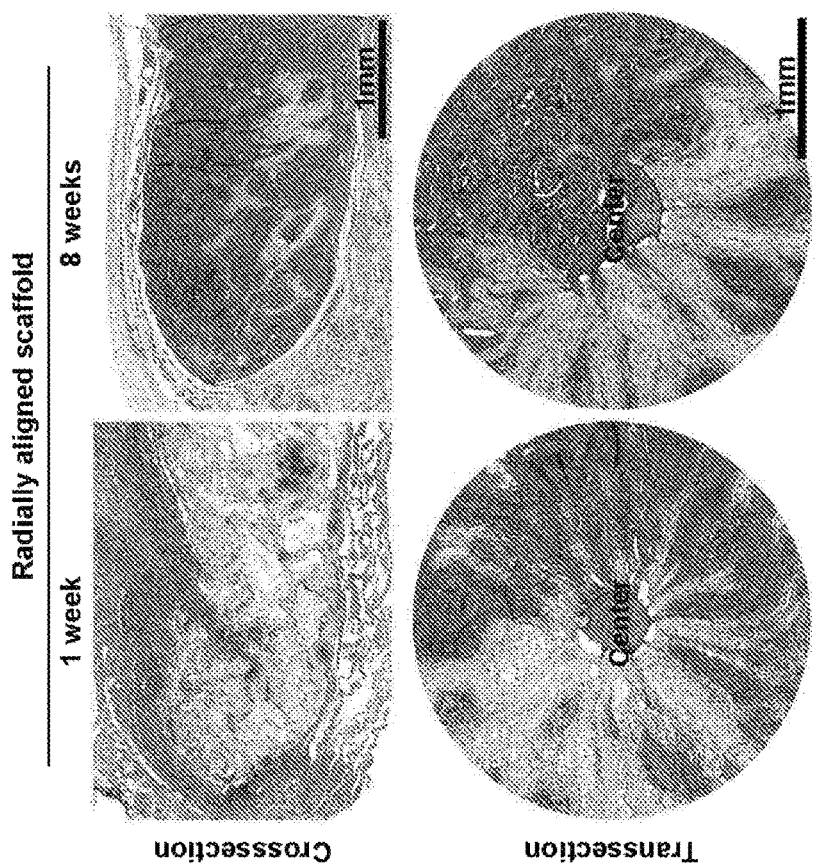
Figure 6D:
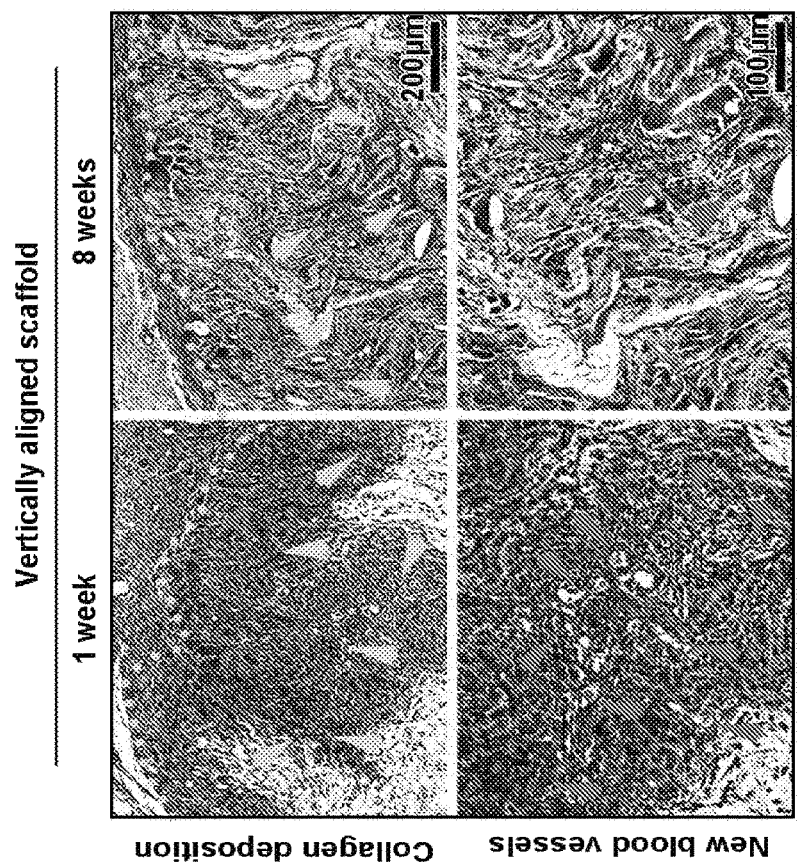
Figure 6C:
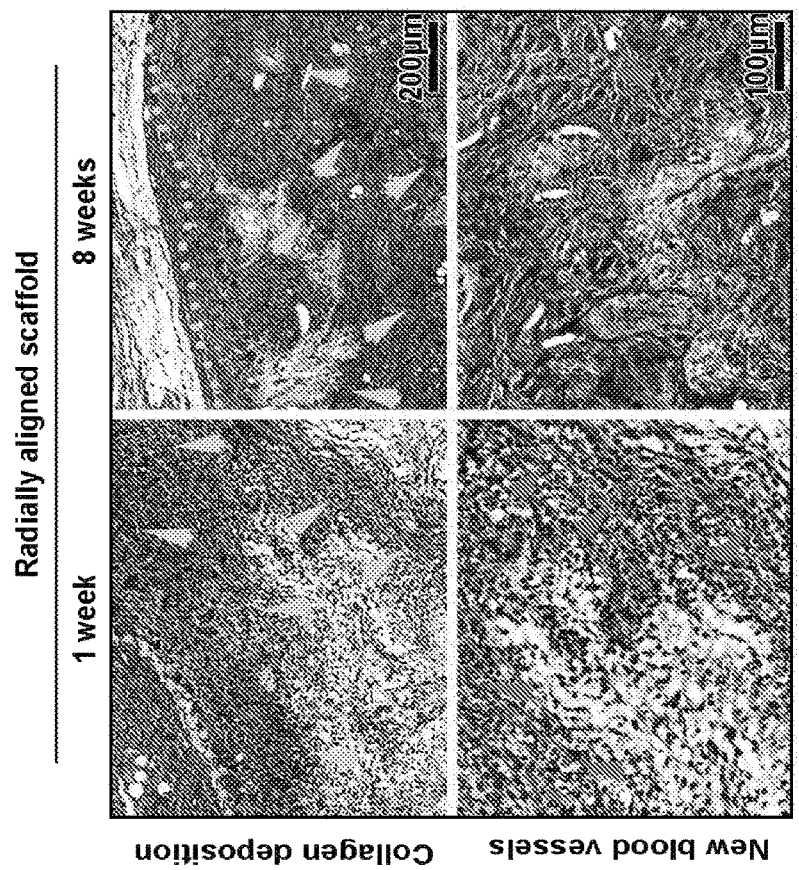
Figure 7B:
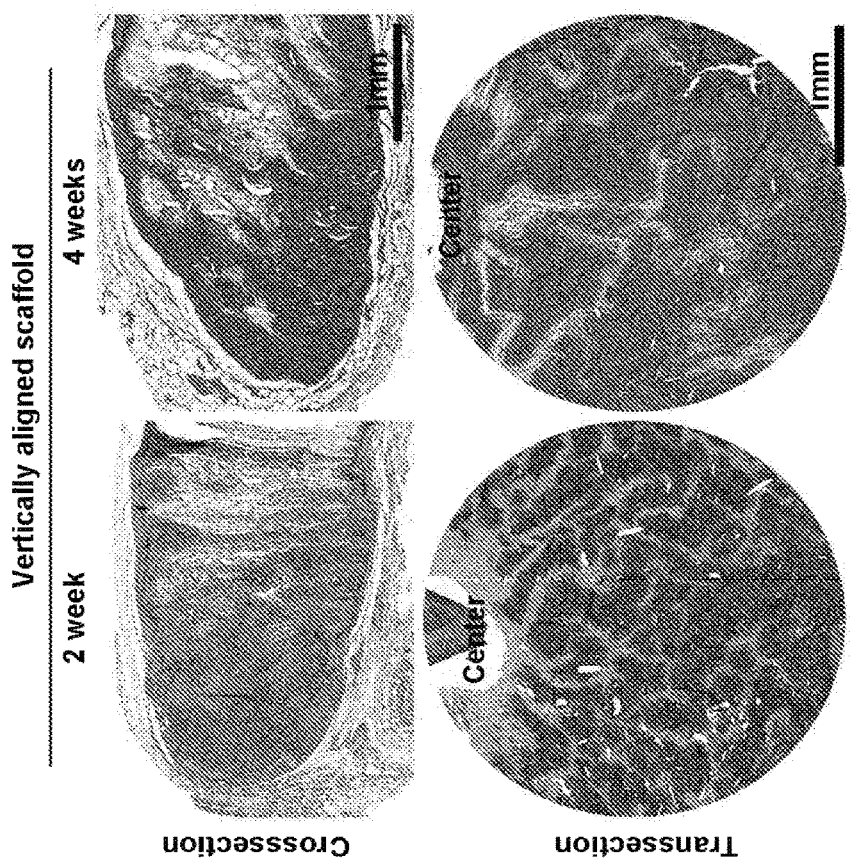
FIGS. 7A-7D shows the in vivo response of expanded, radially-aligned and vertically-aligned PCL nanofiber scaffolds after subcutaneous implantation for 2 and 4 weeks in rats.
Figure 7A:
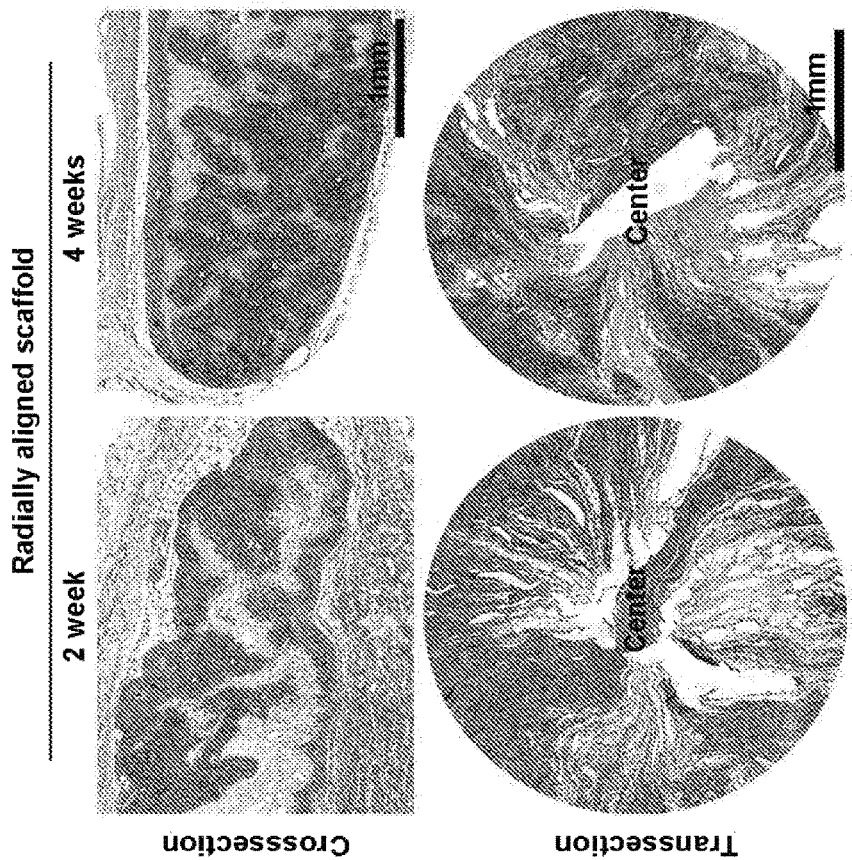
Figure 7D:
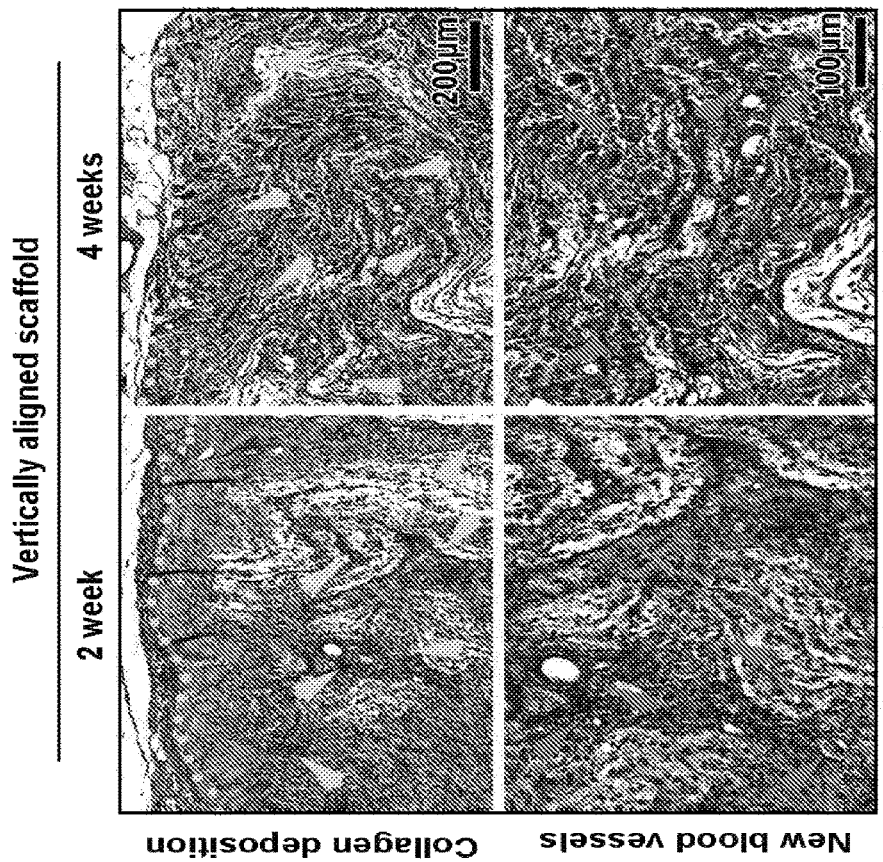
Figure 7C:
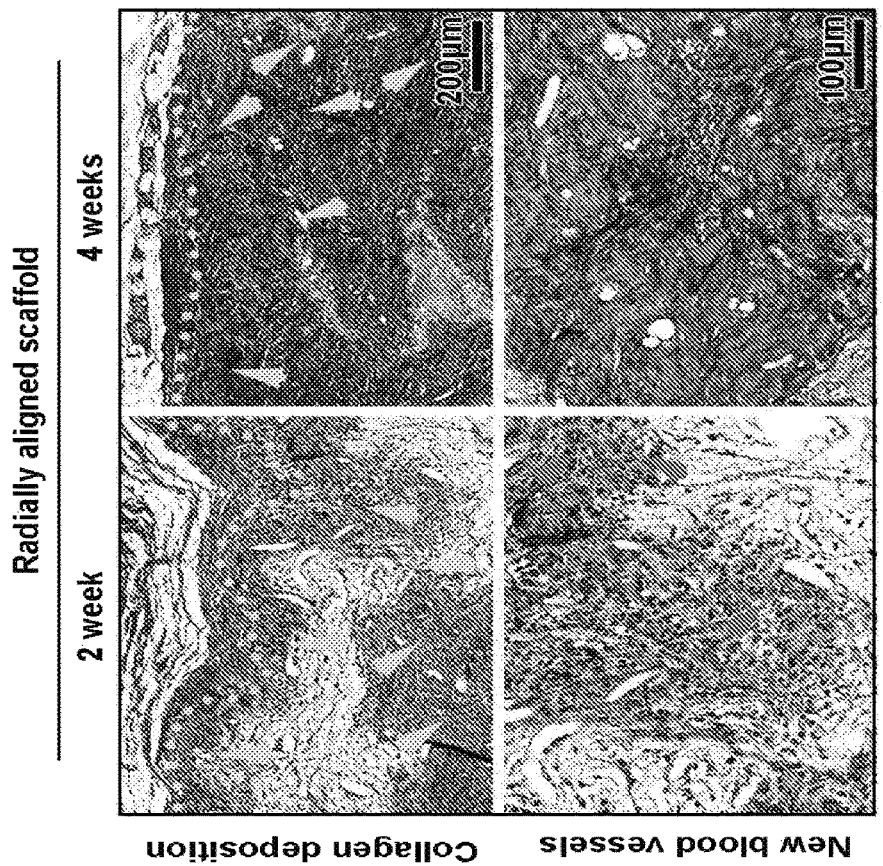

To further demonstrate the in vivo response, 3D nanofiber cylindrical shapes (diameter: 10 mm; height: 1.5 mm) were implanted subcutaneously in rats as acellular scaffolds. Amazingly, H & E staining results showed many cells were infiltrated throughout the shapes just after implantation for 1 week, which was rarely seen for electrospun nanofiber scaffolds (FIGS. 6A, 6B) (Jiang, et al. (2016) Adv. Healthc. Mater., 5:2993-2003). Almost uniform tissues were formed after 8 weeks (FIGS. 6A, 6B). It was noticed that more and more cells were penetrated from 1 week to 8 weeks after implantation (FIGS. 6A, 6B and FIG. 7). It seems that the fiber alignment could help guide the cell infiltration and organization of newly formed tissues (FIGS. 6A, 6B). The rapid cell penetration was attributed to the gaps between the adjacent nanofiber layers, possible cell migration from all sides, top and bottom surfaces, and the contact guidance rendered by aligned nanofibers. Further Masson's trichrome staining showed the corresponding collagen deposition (i.e. ECM production) and new blood vessel formation within the implanted nanofiber cylinders (FIGS. 6C, 6D). Similarly, collagen deposition and blood vessel formation were observed throughout the nanofiber cylinders after implantation for 1 week. It appears that amount of collagen deposition increased with increasing implantation time from 1 week to 8 weeks (FIGS. 6C, 6D and FIG. 7). These results indicate that such nanofiber shapes could rapidly form new tissues through cellular infiltration, ECM deposition, and neovascularization after implantation to the tissue defects.

Figure 8:
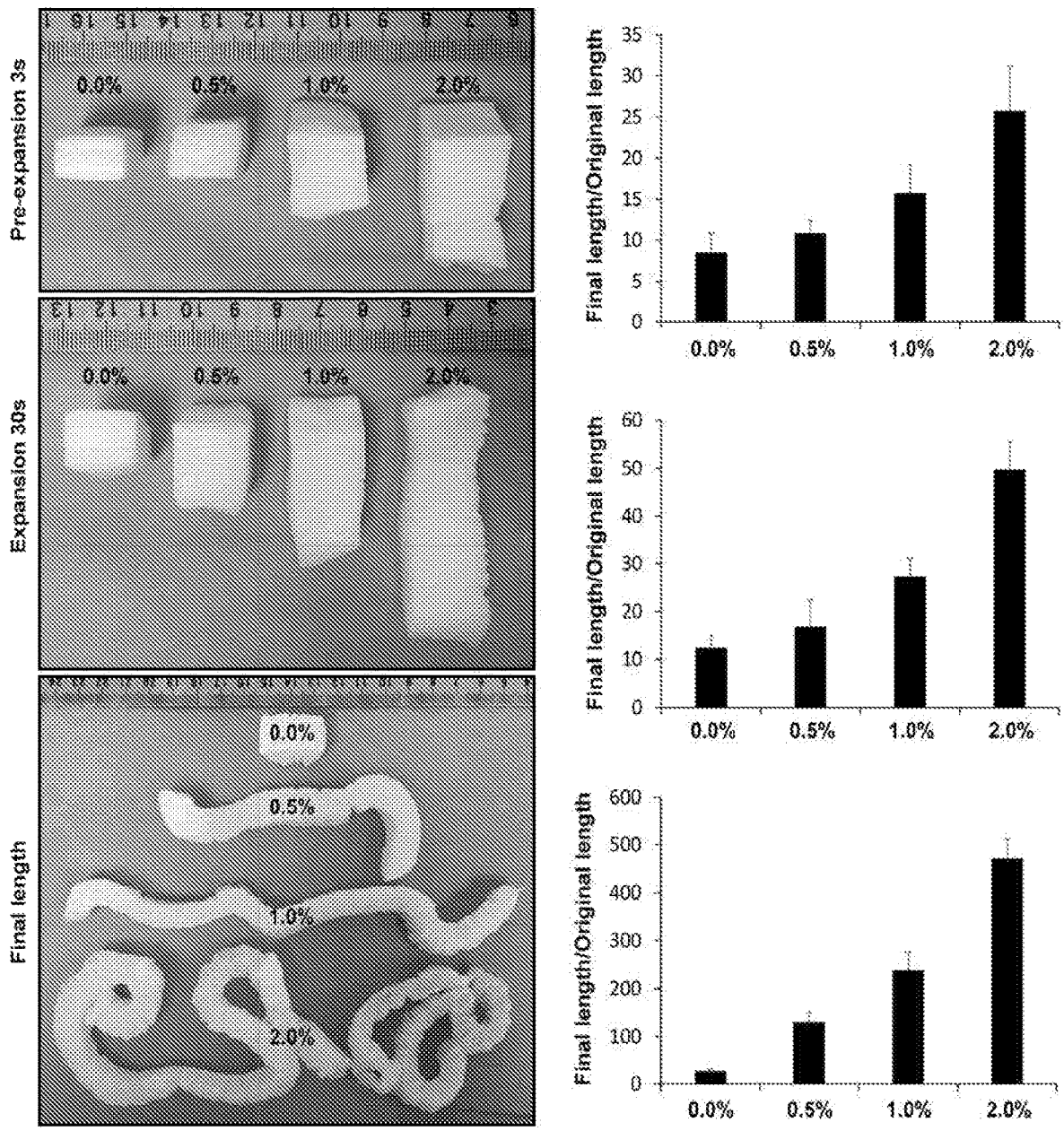
FIG. 8 shows the effect of the incorporation of different amounts of Pluronic® F127 on the expansion process. Images of expanded scaffolds after 3 seconds of expansion, 30 seconds of expansion and full expansion are provided (left). Graphs of the lengths of the scaffold compared to the original length are also provided (right).

Lastly, expanded nanofiber scaffolds with different amounts of surfactants were generated using a modified gas-foaming technique. As seen in FIG. 8, the incorporation of surfactant (e.g., Pluronic® F127) greatly enhance the expansion ratio of nanofiber membranes.

In summary, a novel method has been demonstrated of transforming 2D nanofiber mats to predesigned 3D complex shapes inspired by solids of revolution. These 3D shapes formed highly porous, layered structures and simultaneously retained the nanofiber alignment. Such 3D nanofiber shapes showed shape-recovery property after compression. The 3D shapes were capable of guiding the organization of seeded cells and forming highly ordered 3D tissue constructs. In addition, the 3D shapes promoted cellular infiltration, ECM deposition, and neovascularization after subcutaneous implantation in rats. The 3D shapes fabricated in this study could be useful in other fields (e.g., energy and environment) as well.

Example 2

Figure 9A:
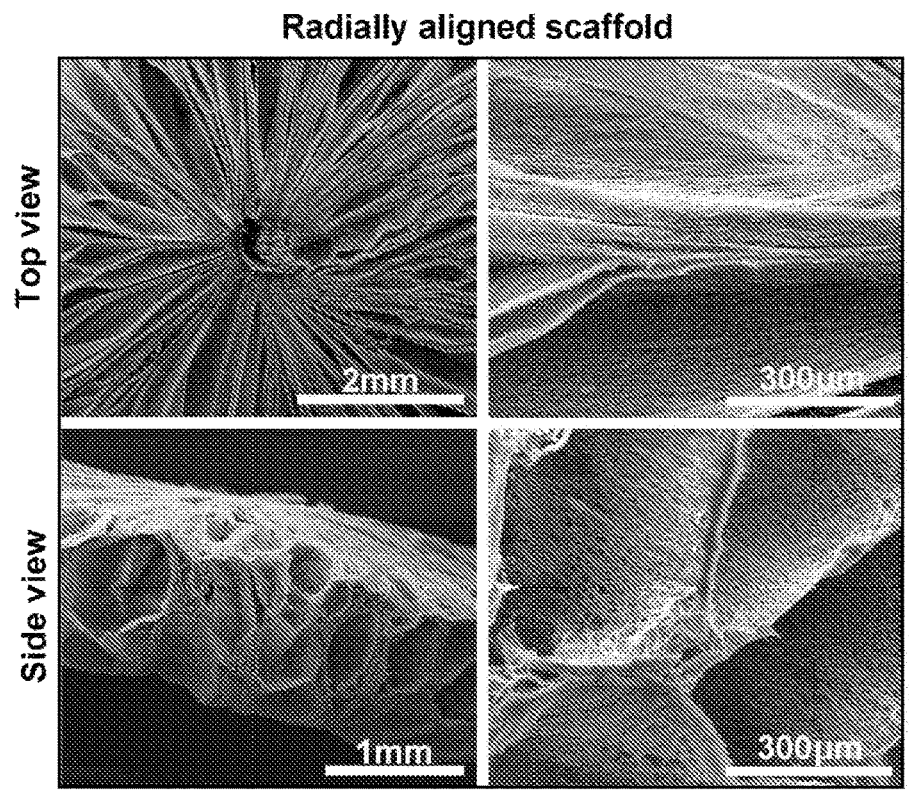
FIGS. 9A and 9B provide SEM images of a radially aligned scaffold and a vertically aligned scaffold, respectively.
Figure 9B:
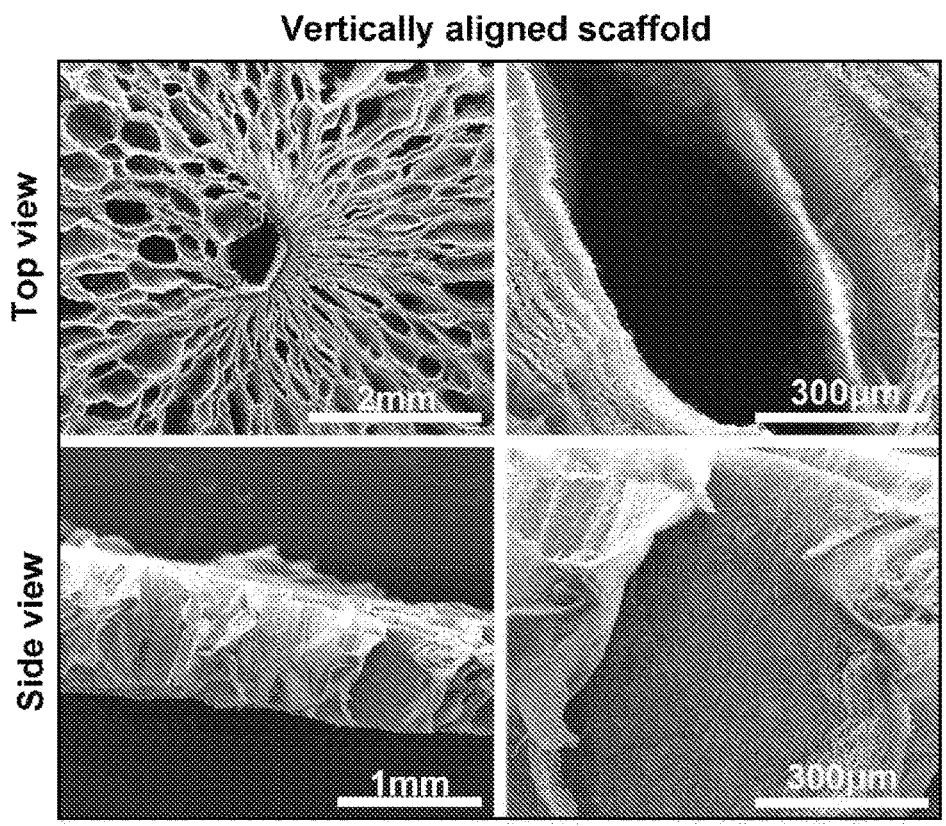

Expanded 3D radially and vertically aligned nanofiber scaffolds using a thermo-fixation and expansion method as described in Example 1 were generated. The morphological characterization using SEM reveals that the top view of the radially aligned scaffold displayed numerous thin layers of radially aligned nanofibers, while the side view exhibited a highly porous structure (FIG. 9A). The top view of the vertically aligned scaffold shows a highly porous structure, and the side view reveals that the pore walls were composed of numerous vertically aligned nanofibers (FIG. 9B). The size, thickness, and shape of these radially and vertically aligned scaffolds can be tailored to match the bone defects.

Figure 10A:
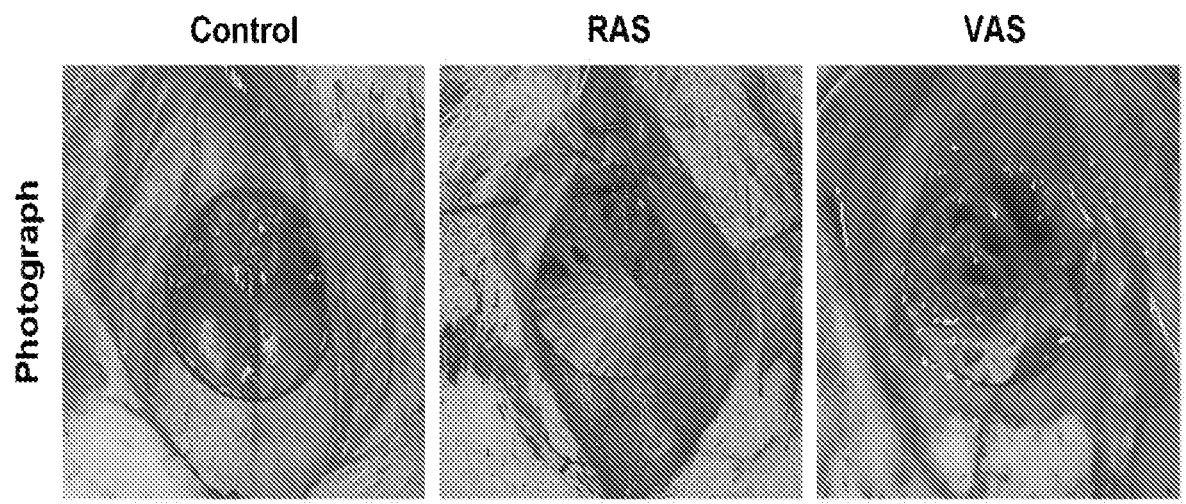
FIGS. 10A-10H show that 3D radially and vertically aligned nanofiber scaffolds promote cranium bone regeneration.
Figure 10B:
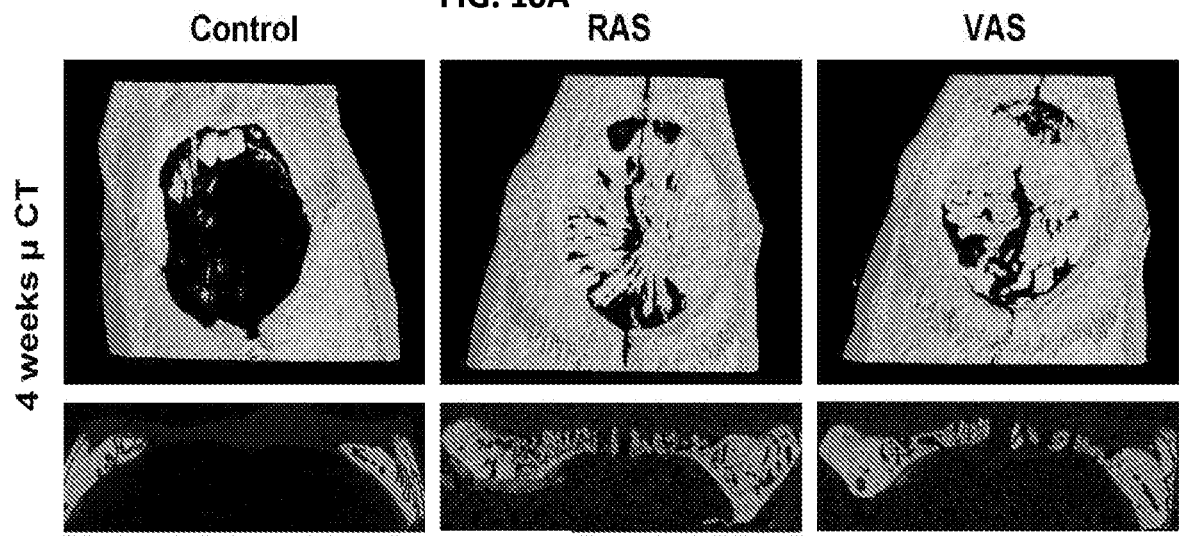
Figure 10C:
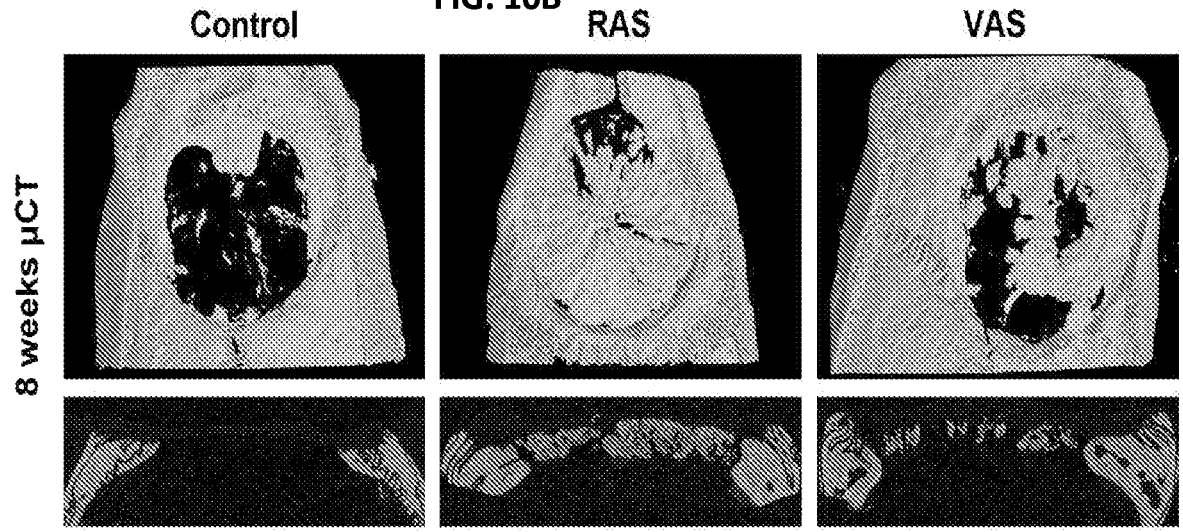
Figure 10D:
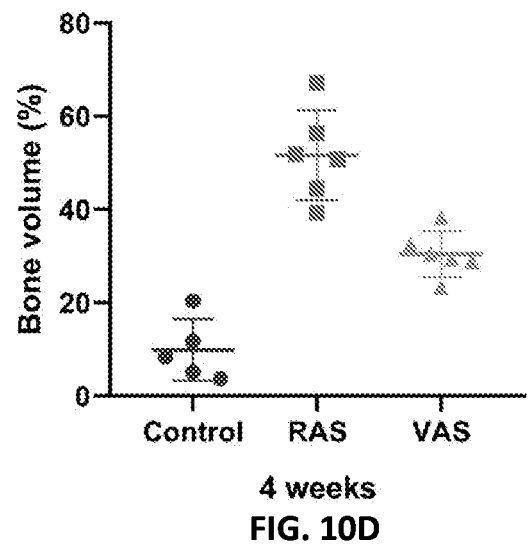
Figure 10E:
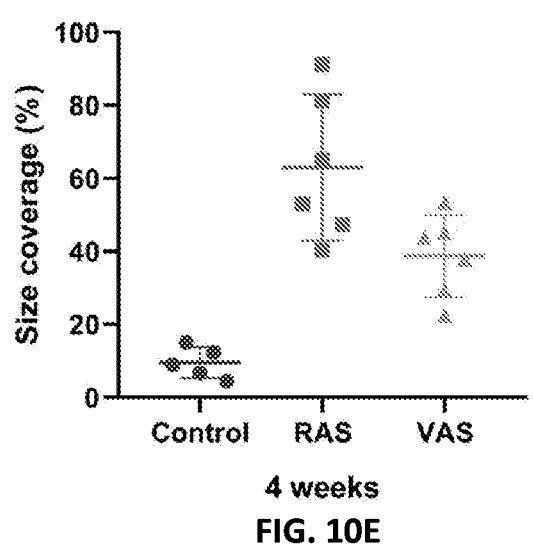
Figure 10F:
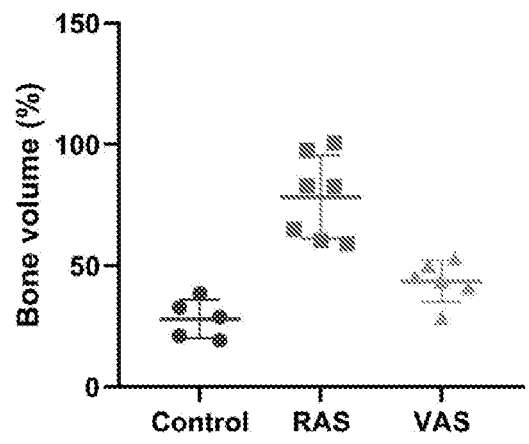
Figure 10G:
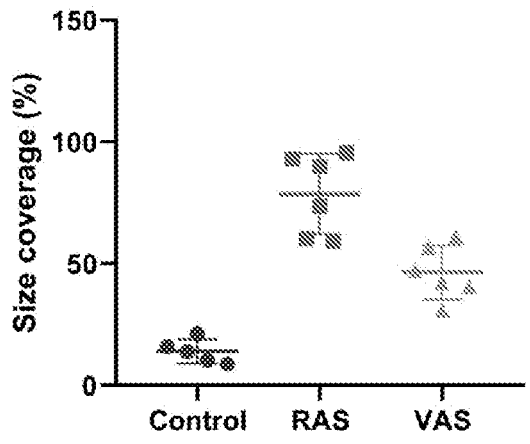
Figure 10H:
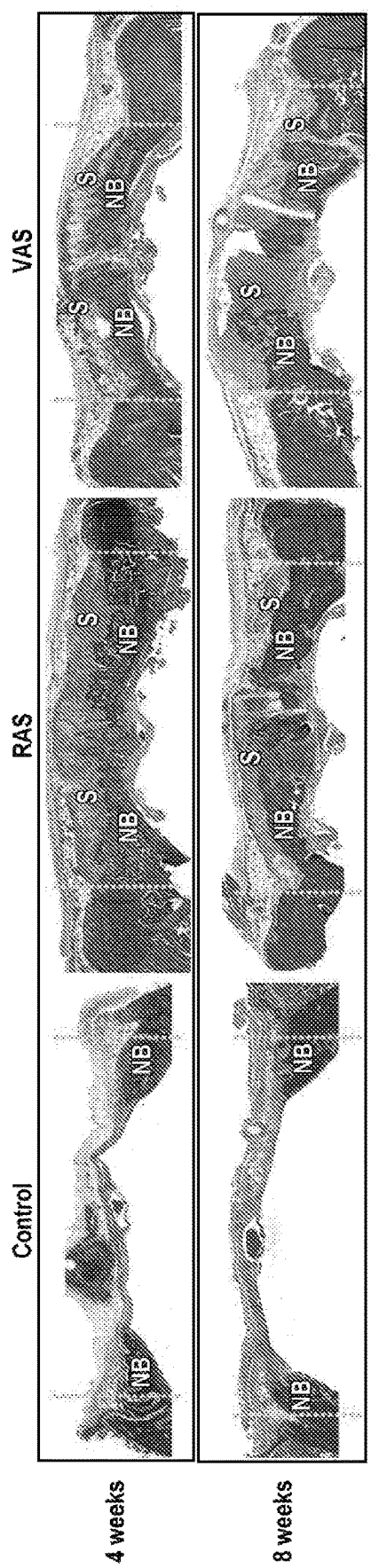

The ability of the scaffolds to regenerate bone in vivo was then tested in a rat model. FIG. 10A provides photographs of the implantation of radially aligned scaffolds (RAS) and vertically aligned scaffolds (VAS). The defect without treatment is shown as control. FIGS. 10B and 10C provide micro computed tomography (micro CT) images of control, RAS and VAS groups at four and eight weeks after implantation, respectively. The bone volume (FIG. 10D) and surface coverage (FIG. 10E) of control, RAS and VAS groups at four weeks after implantation are provided. The bone volume (FIG. 10F) and surface coverage (FIG. 10G) of control, RAS and VAS groups at eight weeks after implantation are also provided. FIG. 10H provides the trichrome staining of control, RAS and VAS groups after 4 and 8 weeks implantation. The results in FIG. 10 clearly show that 3D radially and vertically aligned nanofiber scaffolds promote cranium bone regeneration and that regenerated bone volume of radially and vertically aligned scaffolds groups was significantly higher than the control group after 4- and 8-week implantations. In addition, the surface coverage of radially and vertically aligned groups was also higher than the control group. Notably, both the regenerated bone volume and surface coverage of radially aligned scaffold are higher than vertically aligned scaffold at each indicated time point.

Figure 11A:
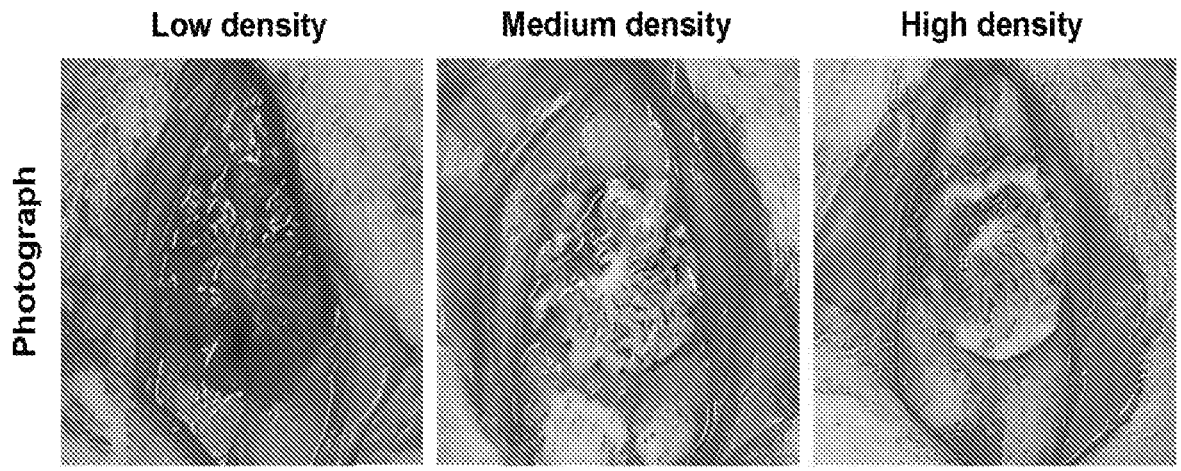
FIGS. 11A-11H show the effects of different densities of vertically aligned nanofiber scaffolds on cranium bone regeneration.
Figure 11B:
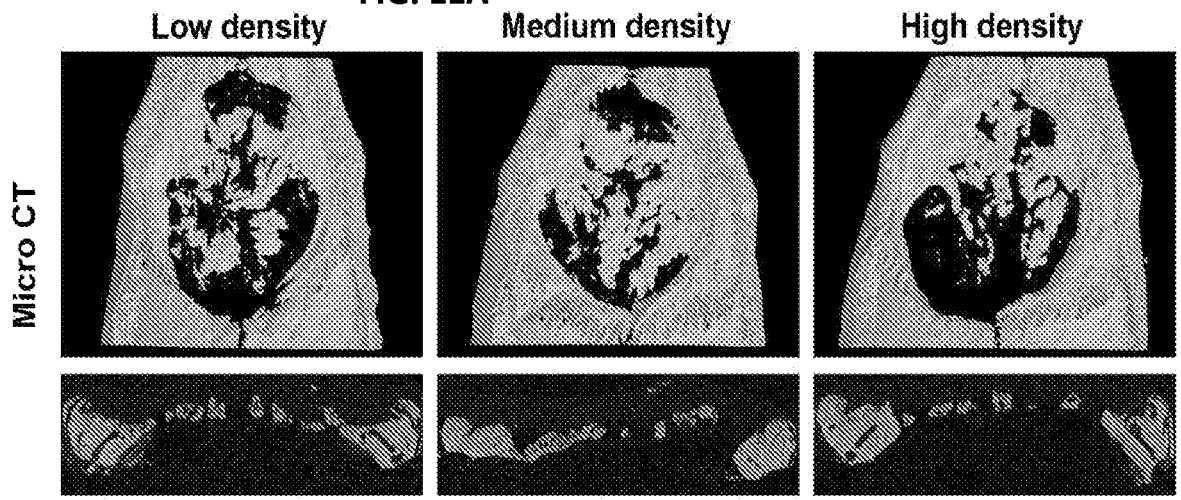
Figure 11C:
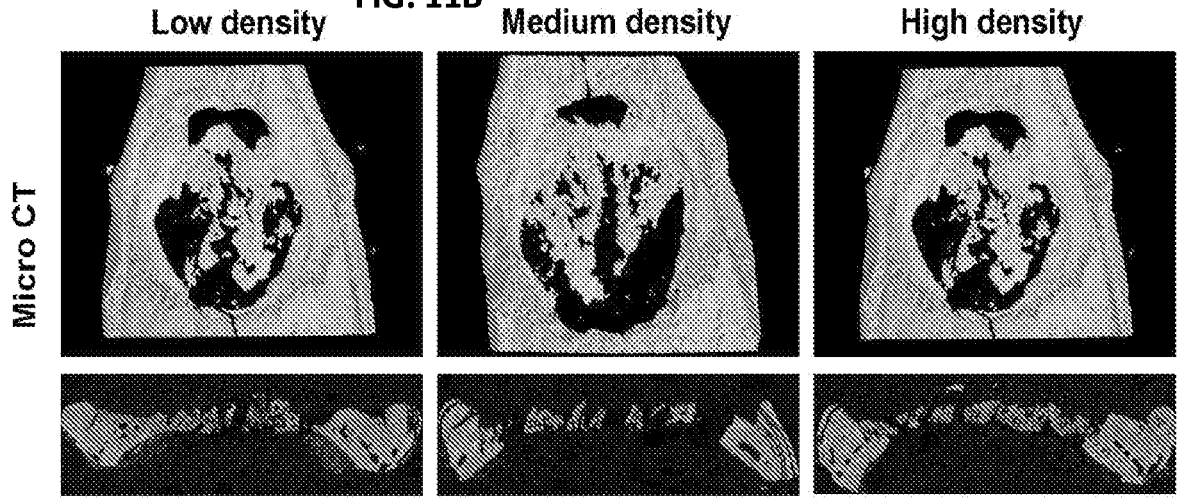
Figure 11D:
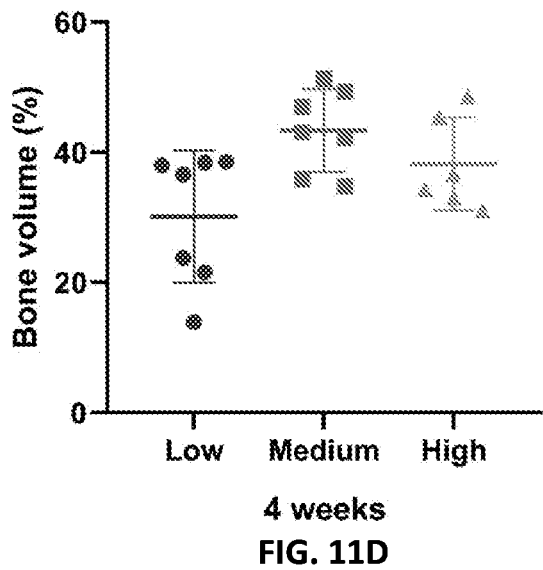
Figure 11E:
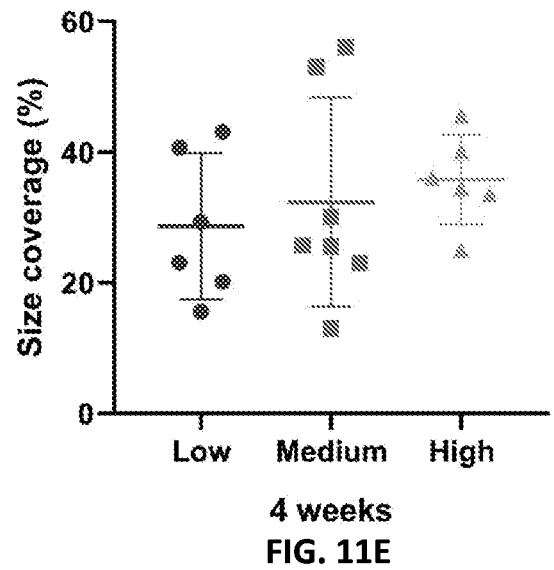
Figure 11F:
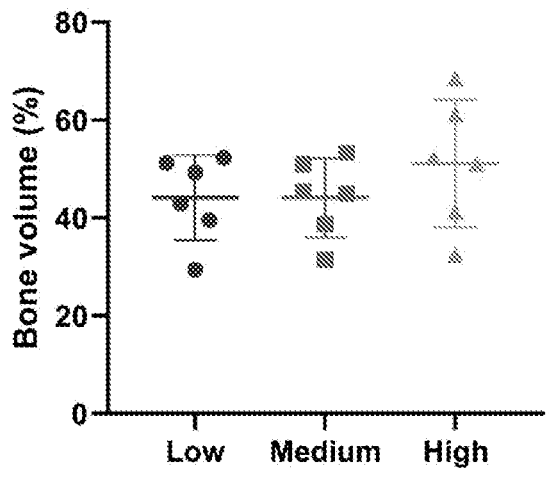
Figure 11G:
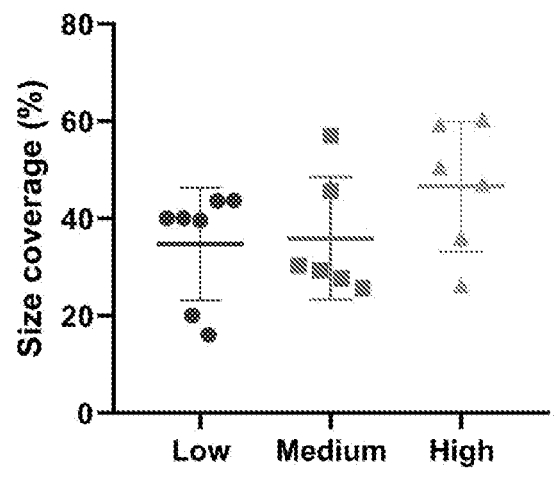
Figure 11H:
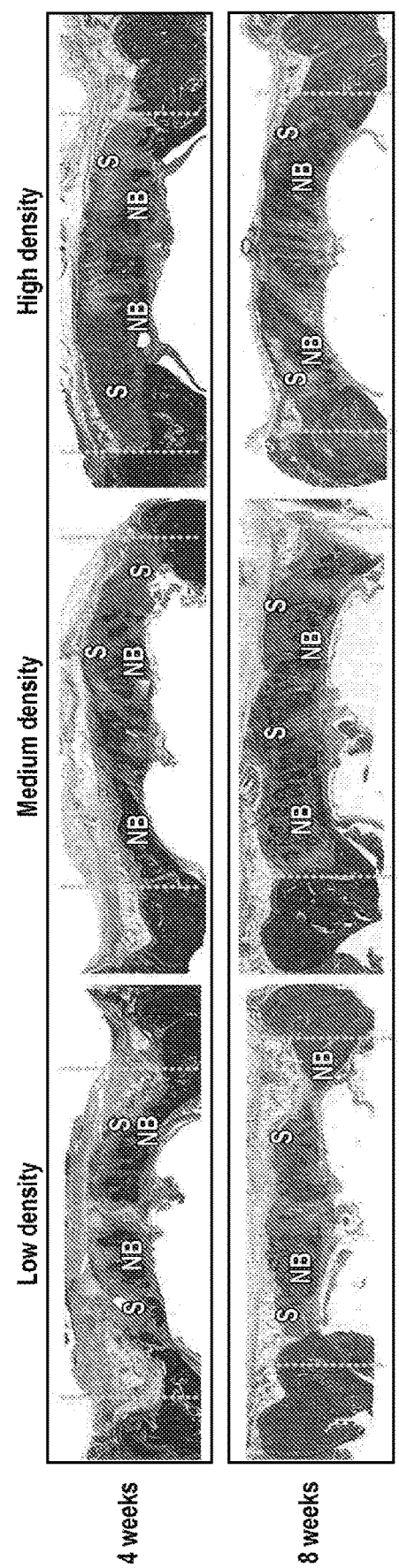

The effect of low density (large pore size), medium density (medium pore size) and high density (small pore size) was also tested. FIG. 11 shows the effects of the different density of vertically aligned nanofiber scaffolds on cranium bone regeneration. FIG. 11A provides photographs of the implantation of low density, medium density and high density of vertically aligned scaffolds. FIGS. 11B and 11C provide micro CT images of low density, medium density and high density of vertically aligned scaffolds treated groups after 4 or 8 weeks of implantation. The bone volume (FIG. 11D) and surface coverage (FIG. 11E) of low density, medium density and high density of vertically aligned scaffolds treated groups after 4 weeks of implantation are provided. The bone volume (FIG. 11F) and surface coverage (FIG. 11G) of low density, medium density and high density of vertically aligned scaffolds treated groups after 8 weeks of implantation are also provided. FIG. 11H provides trichrome staining of low density, medium density and high density of vertically aligned scaffolds treated groups after 4 and 8 weeks implantation. Because of the nanostructure of vertically aligned scaffolds, there was no significant difference in the regenerated bone volume and surface coverage among the low density (large pore size), medium density (Medium pore size) and high density (small pore size) of vertically aligned scaffolds.

Figure 12A:
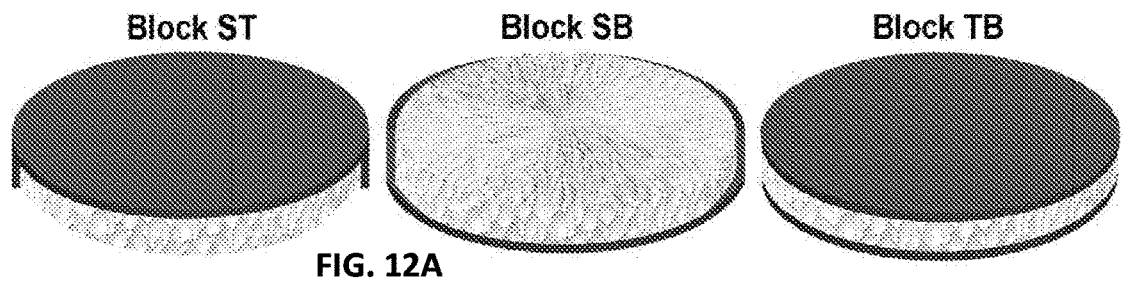
FIGS. 12A-12I show the effects of two side blocked 3D radially aligned scaffolds on cranium bone regeneration.
Figure 12B:
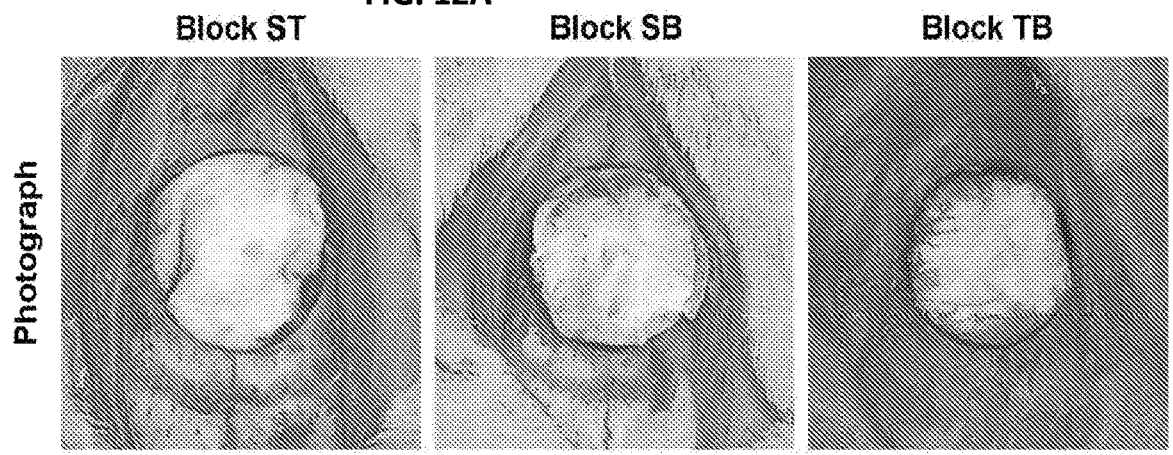
Figure 12C:
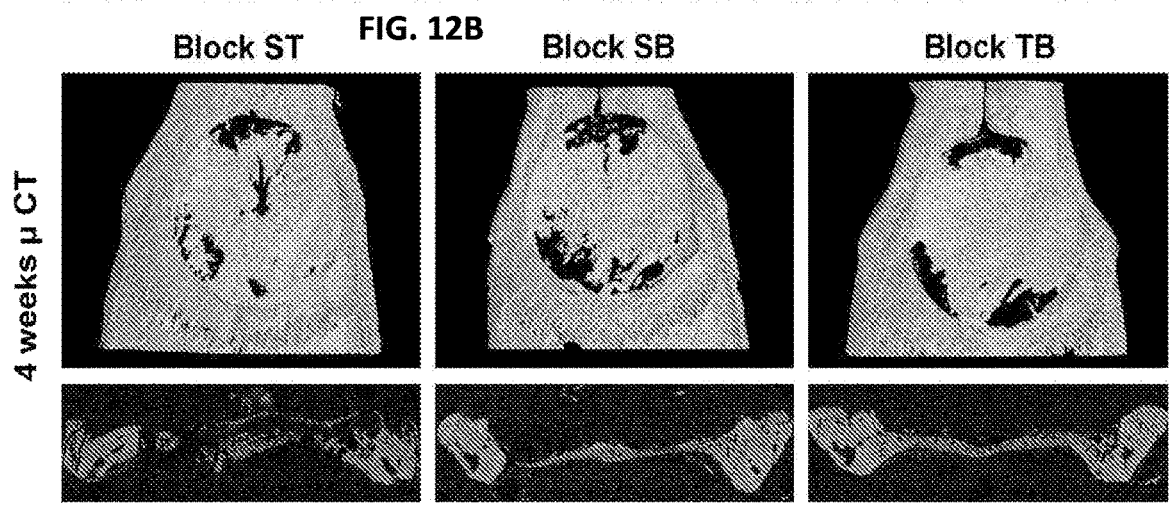
Figure 12D:
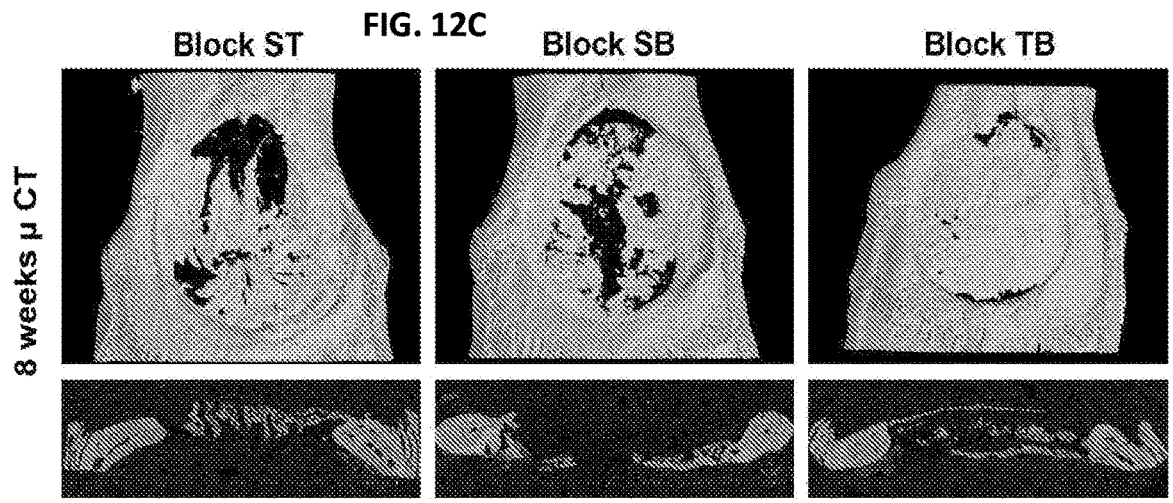
Figure 12E:
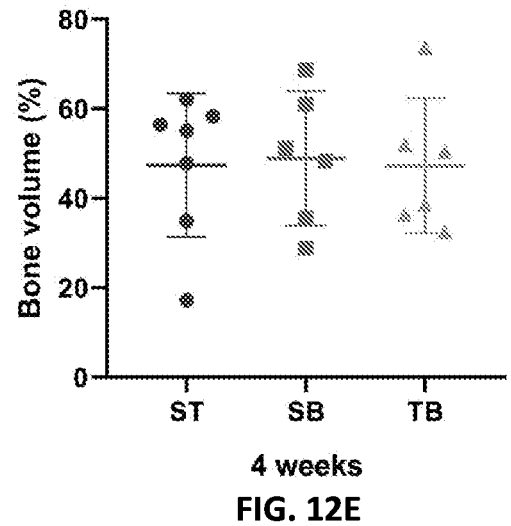
Figure 12F:
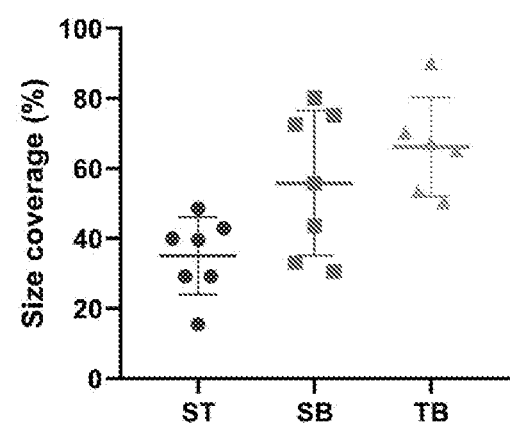
Figure 12G:
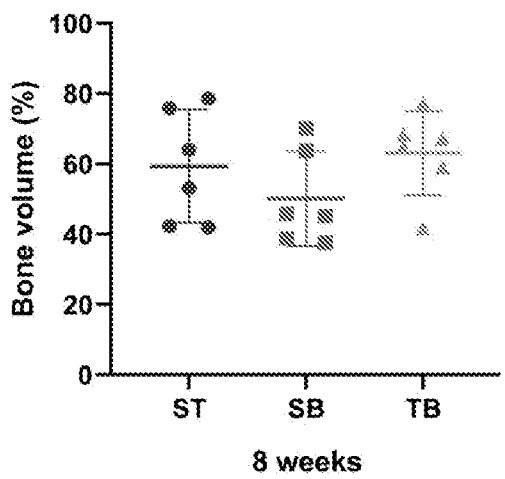
Figure 12H:
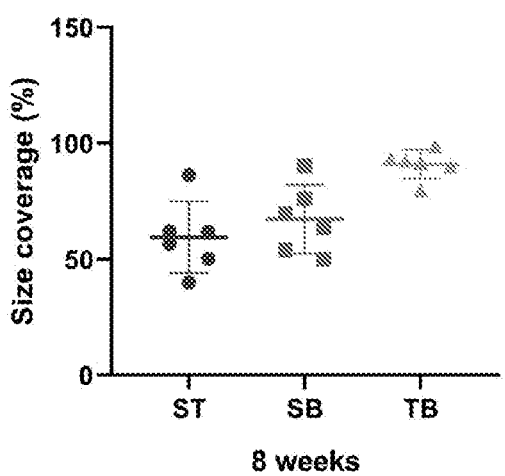
Figure 12I:
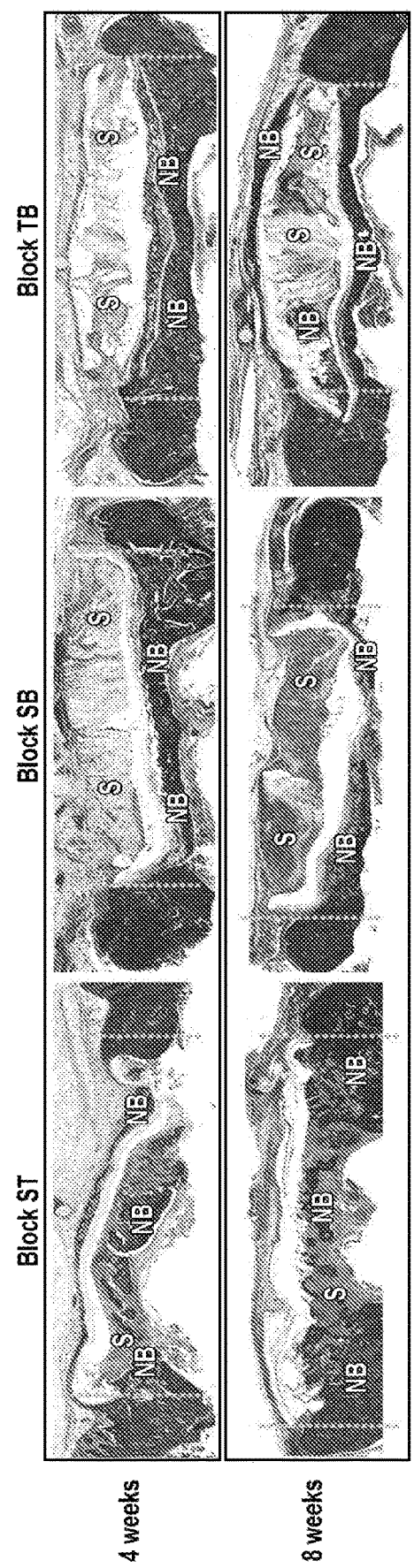

In order to promote cell migration to further boost bone regeneration, aligned nanofiber membrane were used to block the top and bottom sites of radially aligned scaffolds. Scaffolds with blocked surrounding and top sides and scaffolds with blocked surrounding and bottom sides were also used. FIG. 12 shows the effects of two side blocked 3D radially aligned scaffolds on cranium bone regeneration. FIG. 12A provides schematics of different types of two sides blocked 3D radially aligned scaffolds, including blocking the surrounding and top sides (block ST), blocking the surrounding and bottom sides (block SB), blocking the top and bottom sides (block TB). FIG. 12B provides photographs of the implantation of block ST, block SB, and block TB scaffolds. FIGS. 12C and 12D provide micro CT images of block ST, block SB and block TB groups after 4 and 8 weeks of implantation, respectively. The bone volume (FIG. 12E) and surface coverage (FIG. 12F) of block ST, block SB and block TB groups after 4 weeks of implantation are provided. The bone volume (FIG. 12G) and surface coverage (FIG. 12H) of block ST, block SB and block TB groups after 8 weeks of implantation are also provided. FIG. 12I provides trichrome staining of block ST, block SB and Block TB groups after 4 and 8 weeks implantation. By comparison, there was no significant difference in the regenerated bone volume among the 3 groups at both week 4 and week 8. However, the surface coverage of block TB group was higher than block ST and block SB groups on both week 4 and week 8.

These results demonstrate that the expanded nanofiber structures of the instant invention provide high regeneration of bone volume and high surface coverage along with excellent angiogenesis even in the absence of the addition of extra factors such as angiogenesis growth factors.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An expanded nanofiber or microfiber structure, wherein said expanded nanofiber or microfiber structure is an expanded nanofiber or microfiber mat having only one fixed side or a portion thereof.

2. The expanded nanofiber or microfiber structure of claim 1, wherein said nanofiber or microfiber mat comprises electrospun fibers.

3. The expanded nanofiber or microfiber structure of claim 1, wherein said nanofiber or microfiber mat comprises a plurality of uniaxially-aligned nanofibers or microfibers, random nanofibers or microfibers, and/or entangled nanofibers or microfibers.

4. The expanded nanofiber or microfiber structure of claim 1, wherein said nanofiber or microfiber mat comprises polycaprolactone (PCL).

5. The expanded nanofiber or microfiber structure of claim 1, wherein said nanofiber or microfiber mat comprises a poloxamer.

6. The expanded nanofiber or microfiber structure of claim 5, wherein said poloxamer is poloxamer 407.

7. The expanded nanofiber or microfiber structure of claim 1, wherein said fixed side or a portion thereof is thermally fixed.

8. The expanded nanofiber or microfiber structure of claim 1, wherein said fixed side or a portion thereof is chemically fixed.

9. The expanded nanofiber or microfiber structure of claim 1, wherein an entire side of said nanofiber or microfiber mat is fixed.

10. The expanded nanofiber or microfiber structure of claim 1, wherein said expanded nanofiber or microfiber structure is a cylinder, sphere, tube, or hollow sphere.

11. The expanded nanofiber or microfiber structure of claim 1, wherein said expanded nanofiber or microfiber structure comprises an active agent.

12. The expanded nanofiber or microfiber structure of claim 11, wherein said active agent is selected from the group consisting of a therapeutic agent, a growth factor, a signaling molecule, a cytokine, a hemostatic agent, an antimicrobial, and an antibiotic.

13. The expanded nanofiber or microfiber structure of claim 1, wherein said expanded nanofiber or microfiber structure comprises holes or wells.

14. The expanded nanofiber or microfiber structure of claim 1, wherein said expanded nanofiber or microfiber structure is crosslinked.

15. The expanded nanofiber or microfiber structure of claim 1, wherein said expanded nanofiber or microfiber structure further comprises a material selected from the group consisting of gelatin, chitosan, starch, pectin, cellulose, methylcellulose, sodium polyacrylate, and starch-acrylonitrile co-polymers.

16. The expanded nanofiber or microfiber structure of claim 1, wherein at least one side of the expanded nanofiber or microfiber structure is blocked with a nanofiber mat or membrane.

17. The expanded nanofiber or microfiber structure of claim 1, wherein said nanofiber or microfiber mat is expanded by exposing the nanofiber or microfiber mat to gas bubbles.

18. The expanded nanofiber or microfiber structure of claim 1, wherein said nanofiber or microfiber mat has only one melted side or a portion thereof.

19. The expanded nanofiber or microfiber structure of claim 1, wherein said nanofiber or microfiber mat has only one melted side.

20. The expanded nanofiber or microfiber structure of claim 1, wherein said nanofiber or microfiber mat has only one chemically crosslinked side or a portion thereof.

21. The expanded nanofiber or microfiber structure of claim 1, wherein said nanofiber or microfiber mat has only one chemically crosslinked side.

22. The expanded nanofiber or microfiber structure of claim 1, wherein said nanofiber or microfiber mat has only one fixed side.

23. An expanded nanofiber or microfiber structure,
wherein said expanded nanofiber or microfiber structure is an expanded nanofiber or microfiber mat having only one melted side,
wherein said expanded nanofiber or microfiber structure is a cylinder.

24. A method for producing the expanded nanofiber or microfiber structure of claim 1, said method comprising:
a) fixing only one side or a portion thereof of a nanofiber or microfiber mat, and
b) expanding the nanofiber or microfiber mat after step a) by exposing the nanofiber or microfiber mat to gas bubbles,
thereby producing said nanofiber or microfiber structure.

25. The method of claim 24, wherein step b) comprises exposing the nanofiber or microfiber mat to a subcritical fluid and depressurizing.

26. The method of claim 25, wherein said subcritical fluid comprises $CO_2$, $N_2$, $N_2O$, hydrocarbons, or fluorocarbons.

27. The method of claim 25, wherein said subcritical fluid is subcritical $CO_2$.

28. The method of claim 25, wherein said exposure comprises immersing said nanofiber or microfiber mat in said subcritical fluid.

29. The method of claim 24, wherein said nanofiber or microfiber mat comprises electrospun fibers.

30. The method of claim 24, wherein said nanofiber or microfiber mat comprises a plurality of uniaxially-aligned nanofibers or microfibers, random nanofibers or microfibers, and/or entangled nanofibers or microfibers.

31. The method of claim 24, further comprising synthesizing said nanofiber or microfiber mat by electrospinning prior to step a).

32. The method of claim 24, further comprising cutting said nanofiber or microfiber mat prior to step a).

33. The method of claim 24, wherein said nanofiber or microfiber mat comprises polycaprolactone (PCL).

34. The method of claim 24, wherein said nanofiber or microfiber mat comprises a poloxamer.

35. The method of claim 34, wherein said poloxamer is poloxamer 407.

36. The method of claim 24, wherein step a) comprises thermally fixing only one side or a portion thereof of said nanofiber or microfiber mat.

37. The method of claim 24, wherein step a) comprises chemically fixing only one side or a portion thereof of said nanofiber or microfiber mat.

38. The method of claim 24, wherein step a) comprises fixing an entire side of said nanofiber or microfiber mat.

39. The method of claim 24, wherein said nanofiber or microfiber structure is a cylinder, sphere, tube, or hollow sphere.

40. The method of claim 24, wherein said nanofiber or microfiber structure comprises an active agent.

41. The method of claim 40, wherein said active agent is selected from the group consisting of a therapeutic agent, a growth factor, a signaling molecule, a cytokine, a hemostatic agent, an antimicrobial, and an antibiotic.

42. The method of claim 24, wherein said nanofiber or microfiber structure comprises holes or wells.

43. The method of claim 24, further comprising cross-linking the nanofiber or microfiber structure.

44. The method of claim 24, wherein said nanofiber or microfiber structure further comprise a material selected from the group consisting of gelatin, chitosan, starch, pectin, cellulose, methylcellulose, sodium polyacrylate, and starch-acrylonitrile co-polymers.

45. The method of claim 24, further comprising blocking at least one side of the nanofiber or microfiber structure with a nanofiber mat or membrane.

46. A method for producing the nanofiber or microfiber structure of claim 1, said method comprising:
a) thermally fixing only one side or a portion thereof of a nanofiber or microfiber mat, wherein said nanofiber or microfiber mat comprises polycaprolactone (PCL) and a poloxamer, wherein said nanofiber or microfiber mat comprises electrospun fibers, and
b) expanding the nanofiber or microfiber mat after step a) by exposing the nanofiber or microfiber mat to subcritical fluid $CO_2$ and depressurizing,
thereby producing said nanofiber or microfiber structure.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: BMP-2 fragment

<400> SEQUENCE: 1

Lys Ile Pro Lys Ala Ser Ser Val Pro Thr Glu Leu Ser Ala Ile Ser
1               5                   10                  15

Thr Leu Tyr Leu
            20
```